United States Patent

Bennett et al.

[11] Patent Number: 6,015,892
[45] Date of Patent: *Jan. 18, 2000

[54] OLIGONUCLEOTIDE MODULATION OF PROTEIN KINASE C

[75] Inventors: C. Frank Bennett, Carlsbad; Russell T. Boggs, Cardiff; Nicholas M. Dean, Encinitas, all of Calif.

[73] Assignee: ISIS Pharmaceuticals, Inc., Carlsbad, Calif.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/578,615
[22] PCT Filed: Jul. 8, 1994
[86] PCT No.: PCT/US94/07770
§ 371 Date: Jan. 11, 1996
§ 102(e) Date: Jan. 11, 1996
[87] PCT Pub. No.: WO95/02069
PCT Pub. Date: Jan. 19, 1995

Related U.S. Application Data

[63] Continuation of application No. 08/199,779, Feb. 22, 1994, Pat. No. 5,681,747, which is a continuation of application No. 08/089,996, Jul. 9, 1993, Pat. No. 5,703,054, which is a continuation-in-part of application No. 07/852,852, Mar. 16, 1992, abandoned.

[51] Int. Cl.[7] .............. C12Q 1/68; C12N 15/85; C07H 21/04; C07H 21/02
[52] U.S. Cl. .............. 536/24.5; 435/6; 435/91.1; 435/375; 435/91.2; 536/23.1; 536/24.31; 536/24.5; 536/23.5; 514/44
[58] Field of Search .............. 514/44; 536/23.1, 536/23.5, 24.1, 24.5, 24.33, 24.31, 24.3; 435/6

[56] References Cited

U.S. PATENT DOCUMENTS

| | | | |
|---|---|---|---|
| 4,806,463 | 2/1989 | Goodchild et al. | 435/5 |
| 5,004,810 | 4/1991 | Draper | 536/27 |

(List continued on next page.)

FOREIGN PATENT DOCUMENTS

| | | |
|---|---|---|
| WO 93/13121 | 7/1993 | WIPO. |
| WO 93/20101 | 10/1993 | WIPO. |
| WO 94/29455 | 12/1994 | WIPO. |

OTHER PUBLICATIONS

Orkin et al., "Report and recommendations of the panel to assess the NIH investment in research on gene therapy", issued by the U.S. National Institutes of Health, Dec. 1995.

(List continued on next page.)

*Primary Examiner*—George C. Elliott
*Assistant Examiner*—Janet Lee Epps
*Attorney, Agent, or Firm*—Woodcock Washburn Kurtz Mackiewicz & Norris LLP

[57] ABSTRACT

Compositions and methods are provided for the treatment and diagnosis of diseases associated with protein kinase C. Oligonucleotides are provided which are specifically hybridizable with a PKC gene or mRNA. Oligonucleotides specifically hybridizable with a particular PKC isozyme, set of isozymes or mRNA transcript are provided. Methods of treating conditions amenable to therapeutic intervention by modulating protein kinase C expression with an oligonucleotide specifically hybridizable with a PKC gene or mRNA are disclosed. Compositions and methods are provided for the treatment, detection and diagnosis of diseases associated with protein kinase C alpha and specific transcripts thereof. New nucleic acid sequences are provided which encode 3' untranslated regions of human protein kinase C alpha polynucleotide probes for PKC alpha are also disclosed.

20 Claims, 15 Drawing Sheets

U.S. PATENT DOCUMENTS

| | | |
|---|---|---|
| 5,034,506 | 7/1991 | Summerton et al. .................... 528/391 |
| 5,087,617 | 2/1992 | Smith ........................................ 514/44 |
| 5,098,890 | 3/1992 | Gewirtz et al. ............................ 514/44 |
| 5,135,917 | 8/1992 | Burch ........................................ 514/44 |
| 5,166,195 | 11/1992 | Ecker ........................................ 514/44 |
| 5,194,428 | 3/1993 | Agrawal et al. ........................... 514/44 |
| 5,276,019 | 1/1994 | Cohen et al. .............................. 514/44 |
| 5,286,717 | 2/1994 | Cohen et al. .............................. 514/44 |
| 5,620,963 | 4/1997 | Cook et al. ................................ 514/44 |
| 5,681,747 | 10/1997 | Boggs et al. ............................ 435/375 |
| 5,703,054 | 12/1997 | Bennett et al. ............................ 514/44 |

OTHER PUBLICATIONS

Rose–John et al., "Molecular cloning of mouse protein kinase C (PKC) cDNA from Swiss 3T3 fibroblasts", Gene 74: 465–471, 1988.

Uhlmann et al., "Antisense oligonucleotides: A new therapeutic principle", Chemical Reviews 90(4): 543–584, Jun. 1990.

James, "Towards gene–inhibition therapy: a review of progress and prospects in the field of antiviral antisense nucleic acids and ribozymes", Antiviral Chemistry & Chemotherapy 2(4): 191–214, 1991.

Gura et al., "Antisense has growing pains", Science 270: 575–577, Oct. 1995.

Bacher et al., "Isolation and Characterization of PKC–L, A New Member of the Protein Kinase C–Related Gene Family Specifically Expressed in Lung, Skin, and Heart", *Molecular and Cellular Biology* 11: 126–133 (1991).

Ballester and Rosen, "Fate of Immunoprecipitable Protein Kinase C in $GH_3$ Cells Treated with Phorbol 12–Myristate 13–Acetate", *Journal of Biological Chemistry* 260: 15194–15199 (1985).

Coussens et al., "Multiple, Distinct Forms of Bouvine and Human Protein Kinase C Suggest Diversity in Cellular Signaling Pathways", *Science* 233: 859–866 (1986).

Endo et al., "Cell Membrane Signaling as Target in Cancer Therapy: Inhibitory Effect of N,N–Dimethyl and N,N,N–Trimethyl Sphingosine Derivatives on in Vitro and in Vivo Growth of Human Tumor Cells in Nude Mice", *Cancer Research* 51: 1613–1618 (1991).

Finkenzeller et al., "Sequence of Human Protein Kinase C α", *Nucl. Acids Res.* 18: 2183 (1990).

Gescher and Dale, "Protein Kinase C—A Novel Target for Rational Anti–Cancer Drug Design?", *Anti–Cancer Drug Design* 4: 93–105 (1989).

Godson et al., "Inhibition of Expression of Protein Kinase C α By Antisense cDNA Inhibits Phorbol Ester–Mediated Arachidonate Release", *J. Biol. Chem* 268: 11946–11950 (1993).

Hegemann and Mahrle, "Biochemical Pharmacology of Protein Kinase C and Its Relevance for Dermatology", *Pharmacology of the Skin*, H. Mukhtar, ed., CRC Press, Boca Raton, FL 357–368 (1992).

Hidaka and Hagiwara, "Pharmacology of the Isoquinoline Sulfonamide Protein Kinase C Inhibitors", *Trends in Pharm. Sci.* 8: 162–164 1987).

Krug et al, "Evidence for Increased Synthesis as Well as Increased Degradation of Protein Kinase C After Treatment of Human Osteosarcoma Cells with Phorbol Ester", *J. Biol. Chem* 262: 11852–11856 (1987).

Kubo et al., "Primary Structures of Human Protein Kinase CβI and βII Differ Only in their C–Terminal Sequences", *FEBS Lett.* 223: 138–142 (1987).

Nishizuka, "The Molecular Heterogeneity of Protein Kinase C and Its Implications for Cellular Regulation", *Nature* 334: 661–665 (1988).

Nielsen et al., "Sequence–Selective Recognition of DNA by Strand Displacement with a Thymine–Substituted Polyamide", *Science* 254: 1497–1500 (1991).

Osada et al., "A Phorbol Ester Receptor/Protein Kinase, nPKCη, a New Member of the Protein Kinase C Family Predominantly Expressed in Lung and Skin", *J. Biol. Chem* 265: 22434–22440 (1990).

Parker et al., "The Complete Primary Structure of Protein Kinase C–the Major Phorbol Ester Receptor", *Science* 233: 853–866 (1986).

Rothenberg et al, "Oligodeoxynucleotides as Anti–Sense Inhibitors of Gene Expression: Therapeutic Implications", *J. Natl. Cancer Inst.* 81: 1539–1544 (1989).

Sakanoue et al., "Protein Kinase C Activity as Marker for Colorectal Cancer", *Int. J. Cancer* 48: 803–806 (1991).

Weinstein et al., "Cancer Prevention: Recent Progress and Future Opportunities", *Cancer Res.* (Suppl.) 51: 5080s–5085s (1991).

Young et al., "Down–Regulation of Protein Kinase C is Due to an Increased Rate of Degradation", *Biochem. J.* 244: 775–779 (1987).

Zon, "Oligonucleotide Analogues as Potential Chemotherapeutic Agents", *Pharmaceutical Res.* 5: 539–549 (1988).

Borek et al., "Long–Chain (sphingoid) Bases Inhibit Multistage Carcinogenesis in Mouse C3H/10T1/2 Cells Treated with Radiation and Phorbol 12–Myristate 13–Acetate", *Proc. Natl. Acad. Sci.* 88::1953–1957 (1991).

Greenberg, M.E. in *Current Protocols in Molecular Biology* (F.M. Ausubel et al., eds.) John Wiley and Sons, NY (1987).

Marcus–Sekura, "Techniques for Using Antisense Oligodeoxyribonucleotides to Study Gene Expression", *Analytical Biochemistry* 172: 289–295 (1988).

Frohman, et al., *Proc. Natl. Acad. Sci. U.S.A.* 85:8998–9002 (1988).

Sambrook, J., Fritsch, E., and T. Maniatis (1989). Molecular Cloning: a laboratory manual. Cold Spring Harbor Laboratory, Cold Spring Harbor, N.Y., Ch. 7.

Ahmad et al., "Antisense Expression of Protein Kinase Cα Inhibits the Growth and Tumorigenicity of Human Glioblastoma Cells", *Neurosurg.*, 35:904–908 (1994).

Baxter, et al., "PKC–episilon is involved in granulocyte–macrophage colong–stimulating factor signal transduction: Evidence from microphysiometry and antisense oligonucleotide experiments", *Biochemistry*, 31: 10950–10954 (1992).

Berkowitz, P.T. et al., "Synthesis of 1,2–Dihydro–1—(2deoxy–β–D–Erythro–pentafuranosyl)–2 –Oxopyrazine 4–oxide, a potent analog of deoxyuridine", *J. Med. Chem.*, 16: 183–184 (1985).

Brandt, et al., "District Patters of Expression of Different Protein Kinase CmRNA's in Rat Tissues", *Cell.*, 49:57–63 (1987).

Farese, et al., "Antisense DNA downregulates protein kinase C isozymes (beta and alpha) and insulin–stimulated 2–deoxyglucose uptake in rat adipocytes", *Antisense Res. Dev.*, 1 (1): 35–42 (1991).

Maister, *Bioworld Today*, Apr. 29, 1994, p. 3.

Standaert, et al., 1991, J. Cellular Biochem. (Keystone Symposia on Molecular and Cellular Biology, Jan.18–25 ), Suppl. 15B, p. 26, abstract CA 211.

Maier, et al., "An oligomer targeted against protein kinase C alpha prevents interleukin–1 alpha induction of cycloxygenase expression in human endothelial cells", *Exp. Cell. Res.*, 205 (1): 52–58 (1993).

Simons et al., "Antisense c–myb oligonucleotides inhibit intimal arterial smooth cell accumulation in vivo", *Nature* 359:67–70 (1992).

Watson et al., 1987, in Molecular Biology of The Gene, fourth edition, Benjamin/Cummings Publishing Company, Menlo Park, CA p. 241.

Becker, D. et al., "Differential expression of protein kinase C and cAMP–dependent protein kinase in normal human melanocytes and malignant melanomas", *Oncogene*, 1990, 5, 1133–1139.

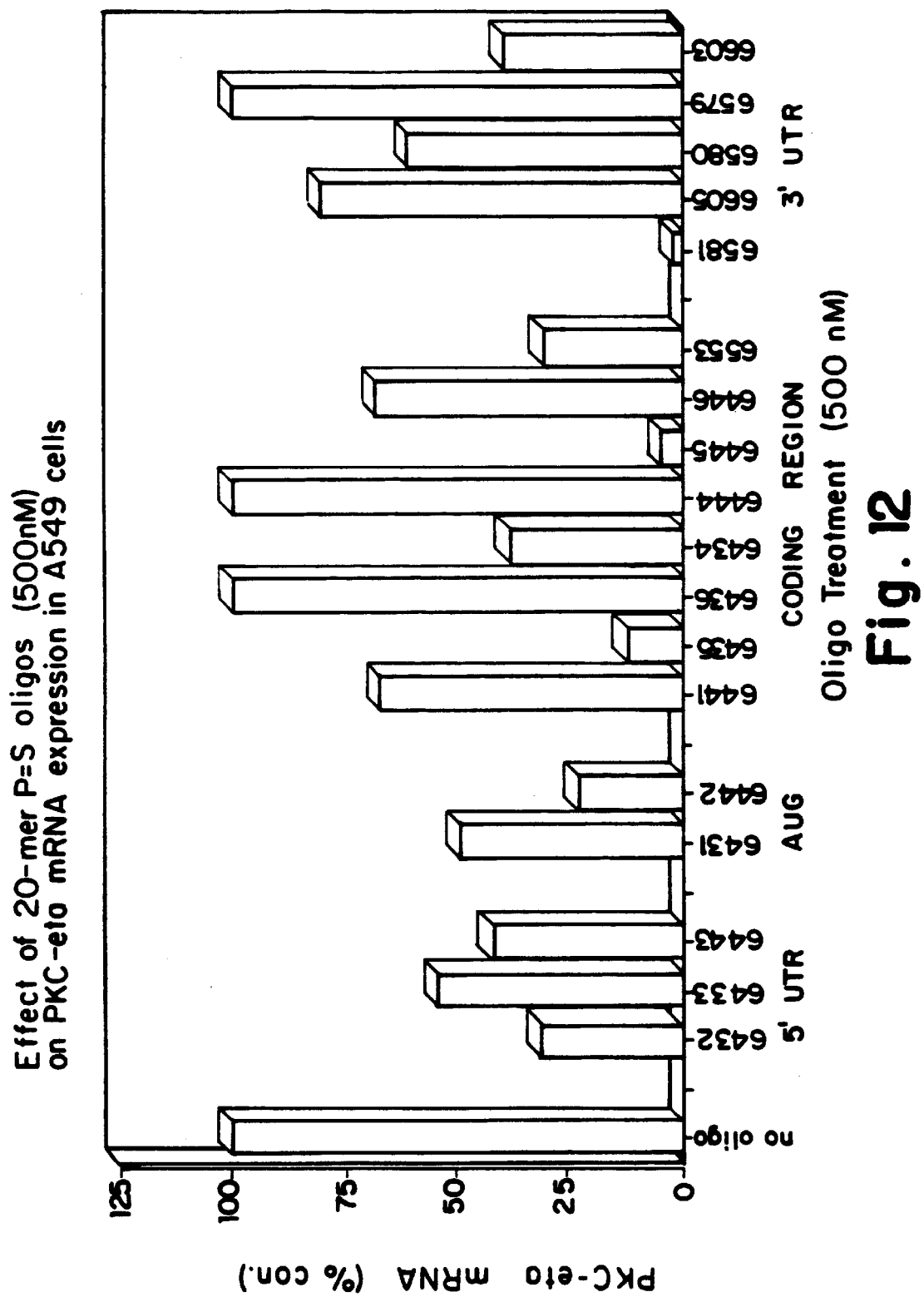

FIGURE 13

| | | | | | | |
|---|---|---|---|---|---|---|
| TGATCAACTG | TTCAGGGTCT | CTCTCTTACA | ACCAAGAACA | TTATCTTAGT | GGAAGATGGT | 60 |
| ACGTCATGCT | CAGTGTCCAG | TTTAATTCTG | TAGAAGTTAC | GTCTGGCTCT | AGGTTAACCC | 120 |
| TTCCTAGAAA | GCAAGCAGAC | TGTTGCCCCA | TTTTGGGTAC | AATTTGATAT | ACTTTCCATA | 180 |
| CCCTCCATCT | GTGGATTTTT | CAGCATTGGA | ATCCCCCAAC | CAGAGATGTT | AAAGTGAGCT | 240 |
| GTCCCAGGAA | ACATCTCCAC | CCAAGACGTC | TTTGAATCC | AAGAACAGGA | AGCCAAGAGA | 300 |
| GTGAGCAGGG | AGGGATTGGG | GGTGGGGGGA | GGCCTCAAAA | TACCGACTGC | GTCCATTCTC | 360 |
| TGCCTCCATG | GAAACAGCCC | CTAGAATCTG | AAAGGCCGGG | ATAAACCTAA | TCACTGTTCC | 420 |
| CAAACATTGA | CAAATCCTAA | CCCAACCATG | GTCCAGCAGT | TACCAGTTTA | AACAAAAAAA | 480 |
| ACCTCAGATG | AGTGTTGGGT | GAATCTGTCA | TCTGGTACCC | TCCTTGGTTG | ATAACTGTCT | 540 |
| TGATACTTTT | CATTCTTTGT | AAGAGGCCAA | ATCGTCTAAG | GACGTTGCTG | AACAAGCGTG | 600 |
| TGAAATCATT | TCAGATCAAG | GATAAGCCAG | TGTGTACATA | TGTTCATTTT | AATCTCTGGG | 660 |
| AGATTATTTT | TCCATCCAGG | GTGCCATCAG | TAATCATGCC | ACTACTCACC | AGTGTTGTTC | 720 |
| GCCAACACCC | ACCCCACAC | ACACCAACAT | TTTGCTGCCT | ACCTTGTTAT | CCTTCTCAAG | 780 |
| AAGCTGAAGT | GTACGCCCTC | TCCCCTTTTG | TGCTTATTTA | TTTAATAGGC | TGCAGTGTCG | 840 |
| CTTATGAAAG | TACGATGTAC | AGTAACTTAA | TGGAAGTGCT | GACTCTAGCA | TCAGCCTCTA | 900 |
| CCGATTGATT | TTCCTCCCTT | CTCTAGCCCT | GGATGTCCAC | TTAGGGATAA | AAAGAATATG | 960 |
| GTTTTGGTTC | CCATTTCTAG | TTCACGTTGA | ATGACAGGCC | TGGAGCTGTA | GAATCAGGAA | 1020 |
| ACCCGGATGC | CTAACAGCTC | AAAGATGTTT | TGTTAATAGA | AGGATTTTAA | TACGTTTTGC | 1080 |
| AAATGCATCA | TGCAATGAAT | TTTGCATGTT | TATAATAAAC | CTTAATAACA | AGTGAATAGA | 1140 |
| AGGATTTTAA | TACGTTTTGC | AAATGCATCA | TGCAATGAAT | TTTGCATGTT | TATAATAAAC | 1200 |
| CTTAATAACA | AGTGAATCTA | TATTATTGAT | ATAATCGTAT | CAAGTATAAA | GAGAGTATTA | 1260 |
| TAATAATTTT | ATAAGACACA | ATTGTGCTCT | ATTTGTGCAG | GTTCTTGTTT | CTAATCCTCT | 1320 |
| TTTCTAATTA | AGTTTTAGCT | GAATCCCTTG | CTTCTGTGCT | TTCCCTCCCT | GCACATGGGC | 1380 |
| ACTGTATCAG | ATAGATTACT | TTTTAAATGT | AGATAAAATT | TCAAAAATGA | ATGGCTAGTT | 1440 |
| TACGTGATAG | ATTAGGCTCT | TACTACATAT | GTGTGTGTAT | ATATATGTAT | TTGATTCTAC | 1500 |
| CTGCAAACAA | ATTTTTATTG | GTGAGGACTA | TTTTTGAGCT | GACACTCCCT | CTTAGTTTCT | 1560 |
| TCATGTCACC | TTTCGTCCTG | GTTCCTCCGC | CACTCTTCCT | CTTGGGACA | ACAGGAAGTG | 1620 |
| TCTGATTCCA | GTCTGGCCTA | GTACGTTGGT | ACACACGTGG | CATTGCGCAG | CACCTGGGCT | 1680 |
| GACCTTTGTG | TGTAGCGTGT | GTGTGTGTTT | CCTTCTTCCC | TTCAGCCTGT | GACTGTTGCT | 1740 |
| GACTCCAGGG | GTGGGAGGGA | TGGGGAGACT | CCCCTCTTGC | TGTGTGTACT | GGACACGCAG | 1800 |
| GAAGCATGCT | GA | | | | | 1812 |

SEQUENCE LISTING (1) GENERAL INFORMATION:

(iii) NUMBER OF SEQUENCES: 122

(2) INFORMATION FOR SEQ ID NO: 1:

(i) SEQUENCE CHARACTERISTICS:
      (A) LENGTH: 20
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 1:

```
CCCCAACCAC CTCTTGCTCC                                                    20

(2) INFORMATION FOR SEQ ID NO: 2:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 2:

GTTCTCGCTG GTGAGTTTCA                                                    20

(2) INFORMATION FOR SEQ ID NO: 3:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 3:

AAAACGTCAG CCATGGTCCC                                                    20

(2) INFORMATION FOR SEQ ID NO: 4:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 4:

GGATTCACTT CCACTGCGGG                                                    20

(2) INFORMATION FOR SEQ ID NO: 5:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 5:

GAGACCCTGA ACAGTTGATC                                                    20

(2) INFORMATION FOR SEQ ID NO: 6:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 6:

CCCGGGAAAA CGTCAGCCAT                                                    20

(2) INFORMATION FOR SEQ ID NO: 7:
```

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 7:

CTGCCTCAGC GCCCCTTTGC                                                   20

(2) INFORMATION FOR SEQ ID NO: 8:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 8:

AGTCGGTGCA GTGGCTGGAG                                                   20

(2) INFORMATION FOR SEQ ID NO: 9:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 9:

GCAGAGGCTG GGGACATTGA                                                   20

(2) INFORMATION FOR SEQ ID NO: 10:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 10:

GGGCTGGGGA GGTGTTTGTT                                                   20

(2) INFORMATION FOR SEQ ID NO: 11:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 11:

CACTGCGGGG AGGGCTGGGG                                                   20

(2) INFORMATION FOR SEQ ID NO: 12:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 12:

AGCCGTGGCC TTAAAATTTT                                          20

(2) INFORMATION FOR SEQ ID NO: 13:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 13:

ATTTTCAGGC CTCCATATGG                                          20

(2) INFORMATION FOR SEQ ID NO: 14:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 14:

AAGAGAGAGA CCCTGAACAG                                          20

(2) INFORMATION FOR SEQ ID NO: 15:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 15:

GATAATGTTC TTGGTTGTAA                                          20

(2) INFORMATION FOR SEQ ID NO: 16:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 16:

ATGGGGTGCA CAAACTGGGG                                          20

(2) INFORMATION FOR SEQ ID NO: 17:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 17:

GTCAGCCATG GTCCCCCCCC                    20

(2) INFORMATION FOR SEQ ID NO: 18:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 18:

CGCCGTGGAG TCGTTGCCCG                    20

(2) INFORMATION FOR SEQ ID NO: 19:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 19:

TCAAATGGAG GCTGCCCGGC                    20

(2) INFORMATION FOR SEQ ID NO: 20:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 20:

TGGAATCAGA CACAAGCCGT                    20

(2) INFORMATION FOR SEQ ID NO: 21:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 21:

CATCTTGCGC GCGGGGAGCC                    20

(2) INFORMATION FOR SEQ ID NO: 22:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 22:

TGCGCGCGGG GAGCCGGAGC                    20

(2) INFORMATION FOR SEQ ID NO: 23:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 23:

CGAGAGGTGC CGGCCCCGGG                                                    20

(2) INFORMATION FOR SEQ ID NO: 24:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 24:

CTCTCCTCGC CCTCCGTCGG                                                    20

(2) INFORMATION FOR SEQ ID NO: 25:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 25:

TGGAGTTTGC ATTCACCTAC                                                    20

(2) INFORMATION FOR SEQ ID NO: 26:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 26:

AAAGGCCTCT AAGACAAGCT                                                    20

(2) INFORMATION FOR SEQ ID NO: 27:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 27:

GCCAGCATGT GCACCGTGAA                                                    20

(2) INFORMATION FOR SEQ ID NO: 28:

(i) SEQUENCE CHARACTERISTICS:
            (A) LENGTH: 20
            (B) TYPE: nucleic acid
            (C) STRANDEDNESS: single
            (D) TOPOLOGY: linear -continued (iv) ANTI-SENSE: yes (xi) SEQUENCE DESCRIPTION: SEQ ID NO: 28:

ACACCCCAGG CTCAACGATG                                              20

(2) INFORMATION FOR SEQ ID NO: 29:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 29:

CCGAAGCTTA CTCACAATTT                                              20

(2) INFORMATION FOR SEQ ID NO: 30:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 30:

ACTTAGCTCT TGACTTCGGG                                              20

(2) INFORMATION FOR SEQ ID NO: 31:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 31:

ATGCTGCGGA AAATAAATTG                                               20

(2) INFORMATION FOR SEQ ID NO: 32:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 32:

ATTTTATTTT GAGCATGTTC                                              20

(2) INFORMATION FOR SEQ ID NO: 33:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 33:

TTTGGGGATG AGGGTGAGCA                                              20

(2) INFORMATION FOR SEQ ID NO: 34:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 34:

CCCATTCCCA CAGGCCTGAG                                              20

(2) INFORMATION FOR SEQ ID NO: 35:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 35:

CGGAGCGCGC CAGGCAGGGA                                              20

(2) INFORMATION FOR SEQ ID NO: 36:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 36:

CCTTTTCCCA GACCAGCCAT                                              20

(2) INFORMATION FOR SEQ ID NO: 37:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 37:

GGCCCCAGAA ACGTAGCAGG                                              20

(2) INFORMATION FOR SEQ ID NO: 38:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 38:

GGATCCTGCC TTTCTTGGGG                                              20

(2) INFORMATION FOR SEQ ID NO: 39:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 39:

CAGCCATGGC CCCAGAAACG                                                   20

(2) INFORMATION FOR SEQ ID NO: 40:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 40:

CGACATGCCG GCGCCGCTGC                                                   20

(2) INFORMATION FOR SEQ ID NO: 41:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 41:

CAGACGACAT GCCGGCGCCG                                                   20

(2) INFORMATION FOR SEQ ID NO: 42:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 42:

GCCTGCTTCG CAGCGGGAGA                                                   20

(2) INFORMATION FOR SEQ ID NO: 43:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 43:

ACAGGTGCAG GAGTCGAGGC                                                   20

(2) INFORMATION FOR SEQ ID NO: 44:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 44:

GTCCCGTCTC AGGCCAGCCC                    20

(2) INFORMATION FOR SEQ ID NO: 45:

(i) SEQUENCE CHARACTERISTICS:
       (A) LENGTH: 20
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO: 45:

CCTCACCGAT GCGGACCCTC                    20

(2) INFORMATION FOR SEQ ID NO: 46:

(i) SEQUENCE CHARACTERISTICS:
       (A) LENGTH: 20
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO: 46:

ATTGAACTTC ATGGTGCCAG                    20

(2) INFORMATION FOR SEQ ID NO: 47:

(i) SEQUENCE CHARACTERISTICS:
       (A) LENGTH: 20
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO: 47:

TCTCACTCCC CATAAGGCTA                    20

(2) INFORMATION FOR SEQ ID NO: 48:

(i) SEQUENCE CHARACTERISTICS:
       (A) LENGTH: 20
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO: 48:

TTCCTTTGGG TTCTCGTGCC                    20

(2) INFORMATION FOR SEQ ID NO: 49:

(i) SEQUENCE CHARACTERISTICS:
       (A) LENGTH: 20
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO: 49:

```
TTCCATCCTT CGACAGAGTT                                                    20

(2) INFORMATION FOR SEQ ID NO: 50:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 50:

AGGCTGATGC TGGGAAGGTC                                                    20

(2) INFORMATION FOR SEQ ID NO: 51:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 51:

GTTCTAAGGC TGATGCTGGG                                                    20

(2) INFORMATION FOR SEQ ID NO: 52:

(i) SEQUENCE CHARACTERISTICS:
          (A) LENGTH: 18
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO:52:

TTCTCGCTGG TGAGTTTC                                                      18

(2) INFORMATION FOR SEQ ID NO: 53:

(i) SEQUENCE CHARACTERISTICS:
          (A) LENGTH: 17
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 53:

TCTCGCTGGT GAGTTTC                                                       17

(2) INFORMATION FOR SEQ ID NO: 54:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 54:

AACTCGAGGT GGCCGCCGTC                                                    20

(2) INFORMATION FOR SEQ ID NO: 55:
```

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO: 55:

CGCCTTCGCA TAGCCCTTTG                                                   20

(2) INFORMATION FOR SEQ ID NO: 56:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO: 56:

GGAAGGGGTG ATTGCGGGCC                                                   20

(2) INFORMATION FOR SEQ ID NO: 57:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO: 57:

AACACGCCCA TTGCCCACCA                                                   20

(2) INFORMATION FOR SEQ ID NO: 58:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO: 58:

GTCTCAAGAT GGCGTGCTCG                                                   20

(2) INFORMATION FOR SEQ ID NO: 59:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO: 59:

GCGATGGTTC AGCTGGGCCC                                                   20

(2) INFORMATION FOR SEQ ID NO: 60:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO: 60:

GCCCTCTCTC TCACTCCCCA                                                   20

(2) INFORMATION FOR SEQ ID NO: 61:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 61:

CTGGGAAGGT CCGATAGAGG                                                   20

(2) INFORMATION FOR SEQ ID NO: 62:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 62:

AAGGCTGATG CTGGGAAGGT                                                   20

(2) INFORMATION FOR SEQ ID NO: 63 :

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 63:

CGCCGCTCCC TTCCATCTTG                                                   20

(2) INFORMATION FOR SEQ ID NO:64 :

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 64:

CCCCGTAATG CGCCTTGAGG                                                   20

(2) INFORMATION FOR SEQ ID NO: 65:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 65:

CTGTCCACCC ACTTGAGGGT                                                     20

(2) INFORMATION FOR SEQ ID NO: 66:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 66:

GCTTCCTCCA TCTTCTGGCT                                                     20

(2) INFORMATION FOR SEQ ID NO: 67:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 67:

CGGTACAGCT TCCTCCATCT                                                     20

(2) INFORMATION FOR SEQ ID NO: 68:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 68:

TTGGAAGAGG TGGCCGTTGG                                                     20

(2) INFORMATION FOR SEQ ID NO: 69:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 69:

CCTGTTAAAG CGCTTGGCTT                                                     20

(2) INFORMATION FOR SEQ ID NO: 70:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 70:

TGCAGGTCAG CGGGACGAGG                                                     20

(2) INFORMATION FOR SEQ ID NO: 71:

(i) SEQUENCE CHARACTERISTICS:
  (A) LENGTH: 20
  (B) TYPE: nucleic acid
  (C) STRANDEDNESS: single
  (D) TOPOLOGY: linear (iv) ANTI-SENSE: yes (xi) SEQUENCE DESCRIPTION: SEQ ID NO: 71:

GCTCTTGGGA AGGCATGACA                    20

(2) INFORMATION FOR SEQ ID NO: 72:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 72:

TTCTTCAACC GCACCAGGAG                    20

(2) INFORMATION FOR SEQ ID NO: 73:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 73:

TTCTTCAACC GCACCAGGAG                    20

(2) INFORMATION FOR SEQ ID NO: 74:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 74:

CTCTGCCTCT GCATGTGGAA                    20

(2) INFORMATION FOR SEQ ID NO: 75:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 75:

TCCTTGCACA TGCCGTAGTC                    20

(2) INFORMATION FOR SEQ ID NO: 76:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 76:

TCCACGCTGA ACCCGTACTC                                                    20

(2) INFORMATION FOR SEQ ID NO: 77:

(i) SEQUENCE CHARACTERISTICS:
                  (A) LENGTH: 20
                  (B) TYPE: nucleic acid
                  (C) STRANDEDNESS: single
                  (D) TOPOLOGY: linear (iv) ANTI-SENSE: yes (xi) SEQUENCE DESCRIPTION: SEQ ID NO: 77:

GGAGCGCCCG GCCATCATCT                                                    20

(2) INFORMATION FOR SEQ ID NO: 78:

(i) SEQUENCE CHARACTERISTICS:
                  (A) LENGTH: 20
                  (B) TYPE: nucleic acid
                  (C) STRANDEDNESS: single
                  (D) TOPOLOGY: linear (iv) ANTI-SENSE: yes (xi) SEQUENCE DESCRIPTION: SEQ ID NO: 78:

GGGCTCGCTG GTGAACTGTG                                                    20

(2) INFORMATION FOR SEQ ID NO: 79:

(i) SEQUENCE CHARACTERISTICS:
                  (A) LENGTH: 20
                  (B) TYPE: nucleic acid
                  (C) STRANDEDNESS: single
                  (D) TOPOLOGY: linear (iv) ANTI-SENSE: yes (xi) SEQUENCE DESCRIPTION: SEQ ID NO: 79:

GACGCACGCG GCCTCACACC                                                    20

(2) INFORMATION FOR SEQ ID NO: 80:

(i) SEQUENCE CHARACTERISTICS:
                  (A) LENGTH: 20
                  (B) TYPE: nucleic acid
                  (C) STRANDEDNESS: single
                  (D) TOPOLOGY: linear (iv) ANTI-SENSE: yes (xi) SEQUENCE DESCRIPTION: SEQ ID NO: 80:

GGGTCAATCA CGCGTGTCCA                                                    20

(2) INFORMATION FOR SEQ ID NO: 81:

(i) SEQUENCE CHARACTERISTICS:
                  (A) LENGTH: 20
                  (B) TYPE: nucleic acid
                  (C) STRANDEDNESS: single
                  (D) TOPOLOGY: linear (iv) ANTI-SENSE: yes (xi) SEQUENCE DESCRIPTION: SEQ ID NO: 81:

TCGGAGCCGT GCCCAGCCTG                                                  20

(2) INFORMATION FOR SEQ ID NO: 82:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 82:

CGGGCCAGGT GTGAGGGACT                                                  20

(2) INFORMATION FOR SEQ ID NO: 83:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 83:

CCGCGACGCA GGCACAGCAG                                                  20

(2) INFORMATION FOR SEQ ID NO: 84:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 84:

TGGAAACCGC ATGACAGCCC                                                  20

(2) INFORMATION FOR SEQ ID NO: 85:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 85:

GGTCAGTGCA TCGAGTTCTG                                                  20

(2) INFORMATION FOR SEQ ID NO: 86:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 86:

ACTACCATGG TCGGGGCGGG                                                  20

(2) INFORMATION FOR SEQ ID NO: 87:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 87:

GTCCCACCGC ATGGCGCAGC                                               20

(2) INFORMATION FOR SEQ ID NO: 88:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 88:

GTTTGGCCGA TGCGCGAGTC                                               20

(2) INFORMATION FOR SEQ ID NO: 89:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 89:

TGCAGTTGGC CACGAAGTCG                                               20

(2) INFORMATION FOR SEQ ID NO: 90:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 90:

GTGGGGCATG TTGACGCTGA                                               20

(2) INFORMATION FOR SEQ ID NO: 91:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 91:

CCAGAGCAGG GACCCACAGT                                               20

(2) INFORMATION FOR SEQ ID NO: 92:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 92:

TCTCCTCGGT TGTCAAATGA                          20

(2) INFORMATION FOR SEQ ID NO: 93:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 93:

CGGTGCTCCT CTCCTCGGTT                          20

(2) INFORMATION FOR SEQ ID NO: 94:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 94:

AGCCAAAATC CTCTTCTCTG                          20

(2) INFORMATION FOR SEQ ID NO: 95:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 95:

CATGAGGGCC GATGTGACCT                          20

(2) INFORMATION FOR SEQ ID NO: 96:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 96:

ATCCCTTCC TTGCACATCCC                          20

(2) INFORMATION FOR SEQ ID NO: 97:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 97:

CCCCAGGGCC CACCAGTCCA        20

(2) INFORMATION FOR SEQ ID NO: 98:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 98:

AGCACCCCCA GGGCCCACCA        20

(2) INFORMATION FOR SEQ ID NO: 99:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 99:

CGTACATCAG CACCCCCAGG        20

(2) INFORMATION FOR SEQ ID NO: 100:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 100:

CCAGCCATCA TCTCGTACAT        20

(2) INFORMATION FOR SEQ ID NO: 101:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 101:

TGCCACACAG CCCAGGCGCA        20

(2) INFORMATION FOR SEQ ID NO: 102:

(i) SEQUENCE CHARACTERISTICS:
          (A) LENGTH: 20
          (B) TYPE: nucleic acid
          (C) STRANDEDNESS: single
          (D) TOPOLOGY: linear (iv) ANTI-SENSE: yes (xi) SEQUENCE DESCRIPTION:  SEQ ID NO: 102:

TCAGGGCATC AGGTCTTCAC        20

(2) INFORMATION FOR SEQ ID NO: 103:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 103:

CTCTCAGGGC ATCAGGTCTT                                                  20

(2) INFORMATION FOR SEQ ID NO:104:

(i) SEQUENCE CHARACTERISTICS:
        (A) LENGTH: 1812 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:104:

TGATCAACTG TTCAGGGTCT CTCTCTTACA ACCAAGAACA TTATCTTAGT GGAAGATGGT        60

ACGTCATGCT CAGTGTCCAG TTTAATTCTG TAGAAGTTAC GTCTGGCTCT AGGTTAACCC       120

TTCCTAGAAA GCAAGCAGAC TGTTGCCCCA TTTTGGGTAC AATTTGATAT ACTTTCCATA       180

CCCTCCATCT GTGGATTTTT CAGCATTGGA ATCCCCCAAC CAGAGATGTT AAAGTGAGCT       240

GTCCCAGGAA ACATCTCCAC CCAAGACGTC TTTGGAATCC AAGAACAGGA AGCCAAGAGA       300

GTGAGCAGGG AGGGATTGGG GGTGGGGGGA GGCCTCAAAA TACCGACTGC GTCCATTCTC       360

TGCCTCCATG GAAACAGCCC CTAGAATCTG AAAGGCCGGG ATAAACCTAA TCACTGTTCC       420

CAAACATTGA CAAATCCTAA CCCAACCATG GTCCAGCAGT TACCAGTTTA AACAAAAAAA       480

ACCTCAGATG AGTGTTGGGT GAATCTGTCA TCTGGTACCC TCCTTGGTTG ATAACTGTCT       540

TGATACTTTT CATTCTTTGT AAGAGGCCAA ATCGTCTAAG GACGTTGCTG AACAAGCGTG       600

TGAAATCATT TCAGATCAAG GATAAGCCAG TGTGTACATA TGTTCATTTT AATCTCTGGG       660

AGATTATTTT TCCATCCAGG GTGCCATCAG TAATCATGCC ACTACTCACC AGTGTTGTTC       720

GCCAACACCC ACCCCCACAC ACACCAACAT TTTGCTGCCT ACCTTGTTAT CCTTCTCAAG       780

AAGCTGAAGT GTACGCCCTC TCCCCTTTTG TGCTTATTTA TTTAATAGGC TGCAGTGTCG       840

CTTATGAAAG TACGATGTAC AGTAACTTAA TGGAAGTGCT GACTCTAGCA TCAGCCTCTA       900

CCGATTGATT TTCCTCCCTT CTCTAGCCCT GGATGTCCAC TTAGGGATAA AAAGAATATG       960

GTTTTGGTTC CCATTTCTAG TTCACGTTGA ATGACAGGCC TGGAGCTGTA GAATCAGGA      1020

ACCCGGATGC CTAACAGCTC AAAGATGTTT TGTTAATAGA AGGATTTTAA TACGTTTTG      1080

AAATGCATCA TGCAATGAAT TTGCATGTT TATAATAAAC CTTAATAACA AGTGAATAG       1140

AGGATTTTAA TACGTTTTGC AAATGCATCA TGCAATGAAT TTGCATGTT TATAATAAA       1200

CTTAATAACA AGTGAATCTA TATTATTGAT ATAATCGTAT CAAGTATAAA GAGAGTATT      1260

TAATAATTTT ATAAGACACA ATTGTGCTCT ATTTGTGCAG GTTCTTGTTT CTAATCCTC      1320

TTTCTAATTA AGTTTTAGCT GAATCCCTTG CTTCTGTGCT TTCCCTCCCT GCACATGGG      1380

ACTGTATCAG ATAGATTACT TTTTAAATGT AGATAAAATT TCAAAAATGA ATGGCTAGT      1440

TACGTGATAG ATTAGGCTCT TACTACATAT GTGTGTGTAT ATATATGTAT TTGATTCTA      1500

CTGCAAACAA ATTTTTATTG GTGAGGACTA TTTTTGAGCT GACACTCCCT CTTAGTTTC      1560

TCATGTCACC TTTCGTCCTG GTTCCTCCGC CACTCTTCCT CTTGGGACA ACAGGAAGT       1620

TCTGATTCCA GTCTGGCCTA GTACGTTGGT ACACACGTGG CATTGCGCAG CACCTGGGC      1680

```
GACCTTTGTG TGTAGCGTGT GTGTGTGTTT CCTTCTTCCC TTCAGCCTGT GACTGTTGC      1740

GACTCCAGGG GTGGGAGGGA TGGGGAGACT CCCCTCTTGC TGTGTGTACT GGACACGCA      1800

GAAGCATGCT GA                                                         1812
```

(2) INFORMATION FOR SEQ ID NO:105:

(i) SEQUENCE CHARACTERISTICS:
        (A) LENGTH: 1757 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:105:

```
ATGGTACGTC ATGCTCAGTG TCCAGTTTAA TTCTGTAGAA GTTACGTCTG GCTCTAGGTT       60

AACCCTTCCT AGAAAGCAAG CAGACTGTTG CCCCATTTTG GGTACAATTT GATATACTTT      120

CCATACCCTC CATCTGTGGA TTTTTCAGCA TTGGAATCCC CCAACCAGAG ATGTTAAAGT      180

GAGCTGTCCC AGGAAACATC TCCACCCAAG ACGTCTTTGA AATCCAAGAA CAGGAAGCCA      240

AGAGAGTGAG CAGGGAGGGA TTGGGGGTGG GGGGAGGCCT CAAAATACCG ACTGCGTCCA      300

TTCTCTGCCT CCATGGAAAC AGCCCCTAGA ATCTGAAAGG CCGGGATAAA CCTAATCACT      360

GTTCCCAAAC ATTGACAAAT CCTAACCCAA CCATGGTCCA GCAGTTACCA GTTTAAACAA      420

AAAAAACCTC AGATGAGTGT TGGGTGAATC TGTCATCTGG TACCCTCCTT GGTTGATAAC      480

TGTCTTGATA CTTTTCATTC TTTGTAAGAG GCCAAATCGT CTAAGGACGT TGCTGAACAA      540

GCGTGTGAAA TCATTTCAGA TCAAGGATAA GCCAGTGTGT ACATATGTTC ATTTTAATCT      600

CTGGGAGATT ATTTTTCCAT CCAGGGTGCC ATCAGTAATC ATGCCACTAC TCACCAGTGT      660

TGTTCGCCAA CACCCACCCC CACACACACC AACATTTTGC TGCCTACCTT GTTATCCTTC      720

TCAAGAAGCT GAAGTGTACG CCCTCTCCCC TTTTGTGCTT ATTTATTTAA TAGGCTGCAG      780

TGTCGCTTAT GAAAGTACGA TGTACAGTAA CTTAATGGAA GTGCTGACTC TAGCATCAGC      840

CTCTACCGAT TGATTTTCCT CCCTTCTCTA GCCCTGGATG TCCACTTAGG GATAAAAAGA      900

ATATGGTTTT GGTTCCCATT TCTAGTTCAC GTTGAATGAC AGGCCTGGAG CTGTAGAATC      960

AGGAAACCCG GATGCCTAAC AGCTCAAAGA TGTTTTGTTA ATAGAAGGAT TTTAATACG      1020

TTTGCAAATG CATCATGCAA TGAATTTTGC ATGTTTATAA TAAACCTTAA TAACAAGTG      1080

ATAGAAGGAT TTTAATACGT TTTGCAAATG CATCATGCAA TGAATTTTGC ATGTTTATA      1140

TAAACCTTAA TAACAAGTGA ATCTATATTA TTGATATAAT CGTATCAAGT ATAAAGAGA      1200

TATTATAATA ATTTTATAAG ACACAATTGT GCTCTATTTG TGCAGGTTCT TGTTTCTAA      1260

CCTCTTTTCT AATTAAGTTT TAGCTGAATC CCTTGCTTCT GTGCTTTCCC TCCCTGCAC      1320

TGGGCACTGT ATCAGATAGA TTACTTTTTA AATGTAGATA AAATTTCAAA AATGAATGG      1380

TAGTTTACGT GATAGATTAG GCTCTTACTA CATATGTGTG TGTATATATA TGTATTTGA      1440

TCTACCTGCA AACAAATTTT TATTGGTGAG GACTATTTTT GAGCTGACAC TCCCTCTTA      1500

TTTCTTCATG TCACCTTTCG TCCTGGTTCC TCCGCCACTC TTCCTCTTGG GGACAACAG      1560

AAGTGTCTGA TTCCAGTCTG GCCTAGTACG TTGGTACACA CGTGGCATTG CGCAGCACC      1620

GGGCTGACCT TTGTGTGTAG CGTGTGTGTG TGTTTCCTTC TTCCCTTCAG CCTGTGACT      1680

TTGCTGACTC CAGGGGTGGG AGGGATGGGG AGACTCCCCT CTTGCTGTGT GTACTGGAC      1740

CGCAGGAAGC ATGCTGA                                                    1757
```

(2) INFORMATION FOR SEQ ID NO:106:

(i) SEQUENCE CHARACTERISTICS:
        (A) LENGTH: 676 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:106:

```
TAGAAGGATT TTAATACGTT TTGCAAATGC ATCATGCAAT GAATTTTGCA TGTTTATAAT      60

AAACCTTAAT AACAAGTGAA TCTATATTAT TGATATAATC GTATCAAGTA TAAAGAGAGT     120

ATTATAATAA TTTTATAAGA CACAATTGTG CTCTATTTGT GCAGGTTCTT GTTTCTAATC     180

CTCTTTTCTA ATTAAGTTTT AGCTGAATCC CTTGCTTCTG TGCTTTCCCT CCCTGCACAT     240

GGGCACTGTA TCAGATAGAT TACTTTTTAA ATGTAGATAA AATTTCAAAA ATGAATGGCT     300

AGTTTACGTG ATAGATTAGG CTCTTACTAC ATATGTGTGT GTATATATAT GTATTTGATT     360

CTACCTGCAA ACAAATTTTT ATTGGTGAGG ACTATTTTTG AGCTGACACT CCCTCTTAGT     420

TTCTTCATGT CACCTTTCGT CCTGGTTCCT CCGCCACTCT TCCTCTTGGG GACAACAGGA     480

AGTGTCTGAT TCCAGTCTGG CCTAGTACGT TGGTACACAC GTGGCATTGC GCAGCACCTG     540

GGCTGACCTT TGTGTGTAGC GTGTGTGTGT GTTTCCTTCT TCCCTTCAGC CTGTGACTGT     600

TGCTGACTCC AGGGGTGGGA GGGATGGGGA GACTCCCCTC TTGCTGTGTG TACTGGACAC     660

GCAGGAAGCA TGCTGA                                                     676
```

(2) INFORMATION FOR SEQ ID NO: 107:

(i) SEQUENCE CHARACTERISTICS:
        (A) LENGTH: 37
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:107:

```
GGCCACGCGT CGACTAGTAC TTTTTTTTTT TTTTTTT                               37
```

(2) INFORMATION FOR SEQ ID NO: 108:

(i) SEQUENCE CHARACTERISTICS:
        (A) LENGTH: 37
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 108:

```
GGGGTAGAAT GCGGCGGCAG TATGAAACTC ACCAGCG                               37
```

(2) INFORMATION FOR SEQ ID NO: 109:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 109:

CAGTGCCCAT GTGCAGGGAG                                    20

(2) INFORMATION FOR SEQ ID NO: 110:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 110:

AGAACCTGCA CAAATAGAGC                                    20

(2) INFORMATION FOR SEQ ID NO: 111:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 111:

AGAAACAAGA ACCTGCACAA                                    20

(2) INFORMATION FOR SEQ ID NO: 112:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 112:

GCAAGGGATT CAGCTAAAAC                                    20

(2) INFORMATION FOR SEQ ID NO: 113:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 113:

AGGGAGGGAA AGCACAGAAG                                    20

(2) INFORMATION FOR SEQ ID NO: 114:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 114:

TCAGCTCAAA AATAGTCCTC                                    20

(2) INFORMATION FOR SEQ ID NO: 115:

```
    (i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 115:

CGAAAGGTGA CATGAAGAAA                                                   20

(2) INFORMATION FOR SEQ ID NO: 116:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 116:

GGCGGAGGAA CCAGGACGAA                                                   20

(2) INFORMATION FOR SEQ ID NO: 117:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 117:

GCAATGCCAC GTGTGTACCA                                                   20

(2) INFORMATION FOR SEQ ID NO: 118:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 118:

TGCAAAACGT ATTAAAATCC                                                   20

(2) INFORMATION FOR SEQ ID NO: 119:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 119:

TTATAAACAT GCAAAATTCA                                                   20

(2) INFORMATION FOR SEQ ID NO: 120:

(i) SEQUENCE CHARACTERISTICS:
        (A) LENGTH: 20
        (B) TYPE: nucleic acid
        (C) STRANDEDNESS: single
        (D) TOPOLOGY: linear
```

```
        (iv) ANTI-SENSE: yes (xi) SEQUENCE DESCRIPTION:  SEQ ID NO: 120:

CCCCAACCAC CTCTTGCTCC                                                      20

(2) INFORMATION FOR SEQ ID NO: 121:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION:  SEQ ID NO: 121:

GTTCTCGCTG GTGAGTTTCA                                                      20

(2) INFORMATION FOR SEQ ID NO: 122:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION:  SEQ ID NO: 122:

GAGACCCTGA CCAGTTGATC                                                      20
```

OLIGONUCLEOTIDE MODULATION OF PROTEIN KINASE C

CROSS REFERENCE TO RELATED APPLICATIONS

This application is the national phase of international Ser. No. PCT/US94/07770 filed Jul. 8, 1994, which is a continuation of Ser. No. 08/199,779 filed Feb. 22, 1994, now U.S. Pat. No. 5,681,747 issued Oct. 28, 1997, which is a continuation of Ser. No. 08/089,996 filed Jul. 9, 1993, now U.S. Pat. No. 5,703,054 issued Dec. 20, 1997, which is a continuation in part of Ser. No. 07/852,852 filed Mar. 16, 1992.

FIELD OF THE INVENTION

This invention relates to therapies, diagnostics, and research reagents for disease states which respond to modulation of the expression of protein kinase C. In particular, this invention relates to antisense oligonucleotides specifically hybridizable with nucleic acids relating to protein kinase C. These oligonucleotides have been found to modulate the expression of protein kinase C. Palliation and therapeutic effect result.

BACKGROUND OF THE INVENTION

The phosphorylation of proteins plays a key role in the transduction of extracellular signals into the cell. The enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells [Gescher et al., *Anti-Cancer Drug Design* 4:93–105 (1989)]. Phorbols capable of tumor production can mimic the effect of DAG in activating PKC, suggesting that these tumor promoters act through PKC and that activation of this enzyme is at least partially responsible for the resulting tumorigenesis [Parker et al., *Science* 233:853–866 (1986)].

Experimental evidence indicates that PKC plays a role in growth control in colon cancer. It is believed that specific bacteria in the intestinal tract convert lipids to DAG, thus activating PKC and altering cell proliferation. This may explain the correlation between high dietary fat and colon cancer [Weinstein, *Cancer Res. (Suppl.)* 51:5080s–5085s (1991)]. It has also been demonstrated that a greater proportion of the PKC in the colonic mucosa of patients with colorectal cancer is in an activated state compared to that of patients without cancer [Sakanoue et al., *Int. J. Cancer* 48:803–806 (1991)].

Increased tumorigenicity is also correlated with overexpression of PKC in cultured cells inoculated into nude mice. A mutant form of PKC induces highly malignant tumor cells with increased metastatic potential.

Sphingosine and related inhibitors of PKC activity have been shown to inhibit tumor cell growth and radiation-induced transformation in vivo [Endo et al., *Cancer Research* 51:1613–1618 (1991); Borek et al., *Proc. Natl. Acad. Sci.* 88:1953–1957 (1991)]. A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs [Gescher, A. and Dale, I.L., *Anti-Cancer Drug Design*, 4:93–105 (1989)].

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions.

Inhibitors of PKC have been shown to have both antiproliferative and antiinflammatory effects in vitro. Some antipsoriasis drugs, such as cyclosporine A and anthralin, have been shown to inhibit PKC. Inhibition of PKC has been suggested as a therapeutic approach to the treatment of psoriasis [Hegemann, L. and G. Mahrle, *Pharmacology of the Skin*, H. Mukhtar, ed., p. 357–368, CRC Press, Boca Raton, Fla., 1992].

PKC is not a single enzyme, but a family of enzymes. At the present time at least seven isoforms (isozymes) of PKC have been identified: $\alpha$, $\beta$, $\gamma$, $\delta$, $\epsilon$, $\zeta$ and $\eta$. These isozymes have distinct patterns of tissue and organ localization (see Nishizuka, *Nature*, 334:661–665 (1988) for review) and may serve different physiological functions. For example, PKC-$\gamma$ seems to be expressed only in the central nervous system. PKC-$\alpha$ and -$\beta$ are expressed in most tissues, but have different patterns of expression in different cell types. For example, both PKC-$\alpha$ and PKC-$\beta$ are expressed in, and have been purified from, human epidermis. While PKC-$\alpha$ has been detected mainly in keratinocytes of the basal layers of the epidermis, PKC-$\beta$ is found mainly in the middle layers of the epidermis and Langerhans cells. PKC-$\eta$ has been found predominantly in the skin and lungs, with levels of expression much higher in these tissues than in the brain. This is in contrast to other members of the PKC family which tend to be most abundantly expressed in the brain [Osada et al., *J. Biol. Chem.* 265:22434–22440 (1990)]. Another PKC isozyme, PKC-$\eta$, is believed to play a critical role in control of proliferative cascades. This was demonstrated by using antisense RNA, peptide inhibitors or a 15-mer phosphorothioate antisense oligonucleotide targeted to the AUG of Xenopus PKC-$\eta$ to deplete PKC-$\eta$ levels in Xenopus oocytes. These depleted oocytes were shown to be resistant to maturation in response to insulin, while the maturation pathway activated by progesterone was not affected. WO 93/20101. While the PKC isozymes listed here are preferred for targeting by the present invention, other isozymes of PKC are also comprehended by the present invention.

It is presently believed that different PKC isozymes may be involved in various disease processes depending on the organ or tissue in which they are expressed. For example, in psoriatic lesions there is an alteration in the ratio between PKC-$\alpha$ and PKC-$\beta$, with preferential loss of PKC-$\beta$ compared to normal skin [Hegemann, L. and G. Mahrle, *Pharmacology of the Skin*, H. Mukhtar, ed., p. 357–368, CRC Press, Boca Raton, Fla., 1992].

Even for a given isozyme, there may be multiple RNA transcripts expressed from a single gene. In the case of PKCα, for example, two mRNA transcripts are seen: a long (approximately 8.5 kb) transcript and a short (approximately 4 kb) transcript. Multiple PKCα transcripts are produced from the murine and the bovine PKCα genes as well. The ratio between the long and short transcripts varies between species and is believed to vary between tissues as well. In addition, there may be some correlation between this ratio and the proliferative state of cells.

Although numerous compounds have been identified as PKC inhibitors (see Hidaka and Hagiwara, *Trends in Pharm. Sci.* 8:162–164 (1987) for review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the CAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases [Gescher, *Anti-Cancer Drug Design* 4:93–105 (1989)]. Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and as treatment for diseases which may be associated with particular isozymes. Godson et al. [*J. Biol. Chem.* 268:11946–11950 (1993)] recently disclosed use of stable transfection of antisense PKC-α cDNA in cytomegalovirus promotor-based expression vectors to specifically decrease expression of PKC-α protein by approximately 70%. It was demonstrated that this inhibition causes a loss of phospholipase A$_2$-mediated arachidonic acid release in response to the phorbol ester PMA. Attempts by the same researchers at inhibiting PKC activity with oligodeoxynucleotides were ultimately unsuccessful due to degradation of oligonucleotides.

OBJECTS OF THE INVENTION

It is a principal object of the invention to provide therapies for neoplastic, hyperproliferative, inflammatory and other disease states associated with protein kinase C.

Another object of the invention is to provide selective therapies for diseases associated with particular isozymes of protein kinase C.

It is a further object of the invention to provide antisense oligonucleotides which are capable of modulating the expression of protein kinase C.

Another object of the invention is to provide antisense oligonucleotides which are capable of selectively modulating the expression of particular isozymes of protein kinase C.

Yet another object is to provide means for diagnosis of diseases associated with protein kinase C.

A further object of the invention is to provide means for differential diagnosis of diseases associated with particular isozymes of protein kinase C.

A still further object of the invention is to provide research tools for the study of the effects of protein kinase C expression and diseases associated therewith.

An additional object of the invention is to provide research tools for the study of the effects of expression of particular isozymes of protein kinase C and diseases associated therewith.

It is an object of the invention to provide novel nucleic acid molecules encoding a 3'-untranslated region of human PKCα, including sequences unique to the long mRNA transcript of PKCα.

Another object of the invention is to provide antisense oligonucleotides which are capable of selectively modulating the expression of particular mRNA transcripts of PKCα.

A further object of the invention is to provide polynucleotide probes for detection of human PKC.

A still further object of the invention is to provide polynucleotide probes for detection of particular mRNA transcripts of PKCα.

A further object of the invention is to provide means for differential diagnosis of diseases associated with particular mRNA transcripts of PKCα.

It is an object of the invention to provide therapies for neoplastic, hyperproliferative, inflammatory and other disease states associated with PKCα.

Another object of the invention is to provide selective therapies for diseases associated with particular mRNA transcripts of PKCα.

An additional object of the invention is to provide research tools for the study of the effects of expression of particular transcripts of PKCα and diseases associated therewith.

These and other objects of this invention will become apparent from a review of the instant specification.

Figure 9A:
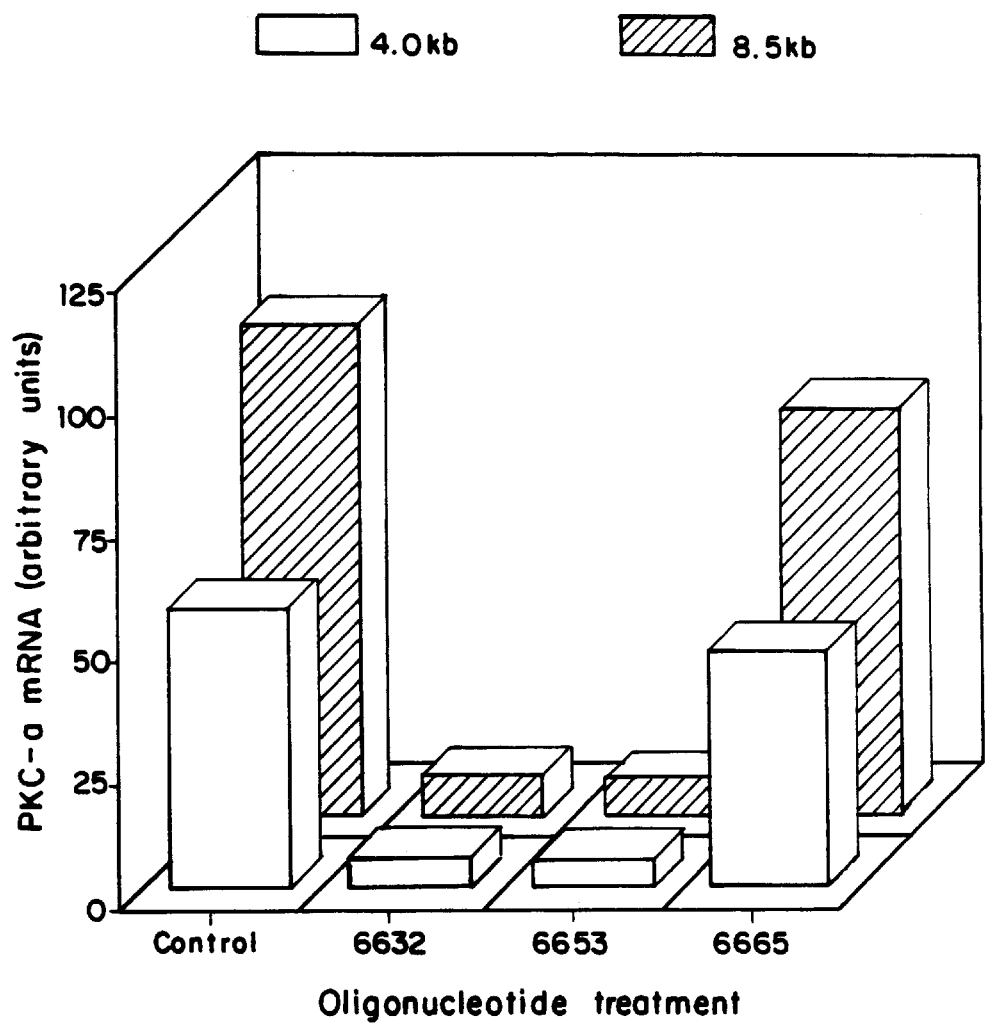
Figure 9B:
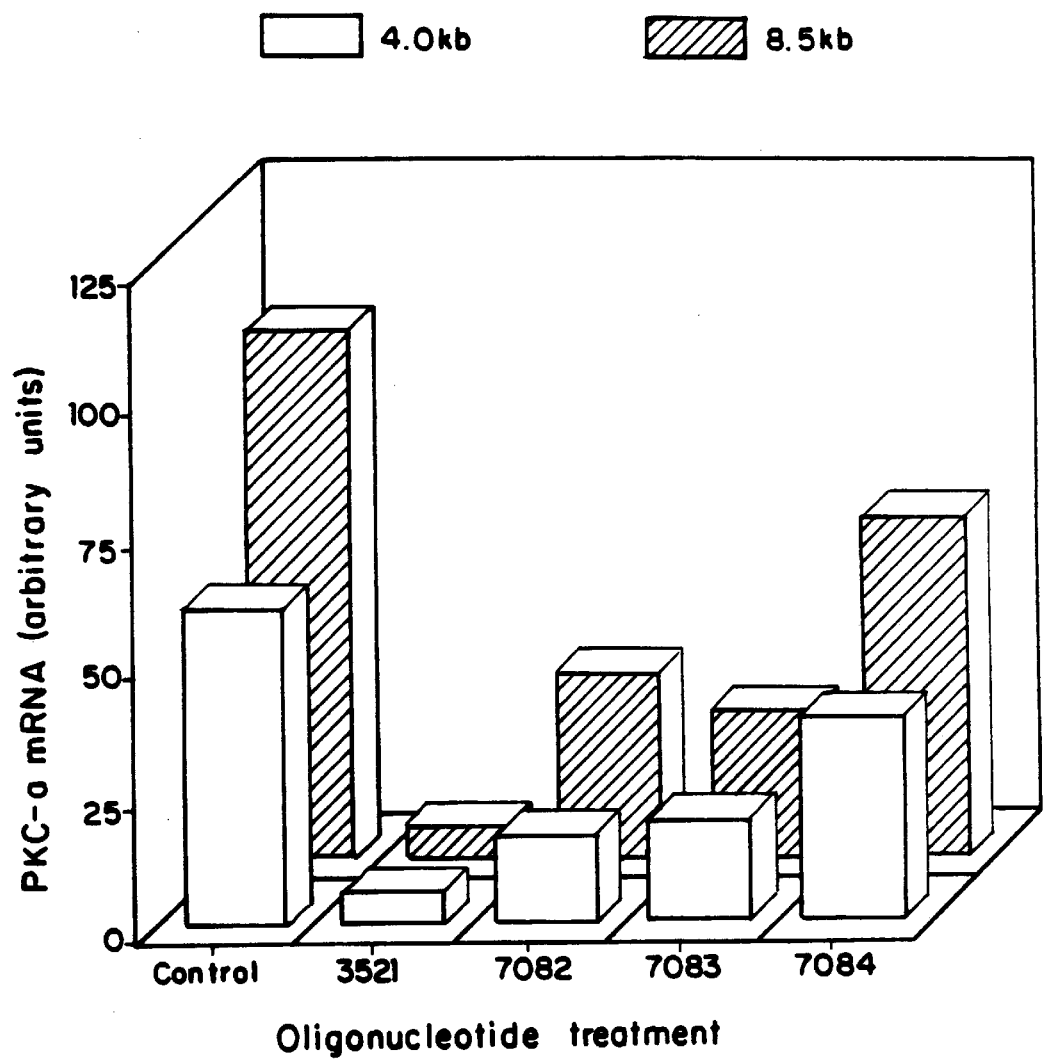

FIGS. 9A and 9B are a set of bar graphs showing the effect of additional oligonucleotides on PKC-α mRNA levels. FIG. 9A shows oligonucleotides 6632 (SEQ ID NO:52), 6653 (SEQ ID NO:52) and 6665. FIG. 9B shows oligonucleotides 3521 (for comparison SEQ ID NO:2), 7082 (SEQ ID NO:53), 7083 (SEQ ID NO:53) and 7084 (SEQ ID NO:53). Hatched bars represent the 8.5 kb transcript, plain bars represent the 4.0 kb transcript.

Figure 10:
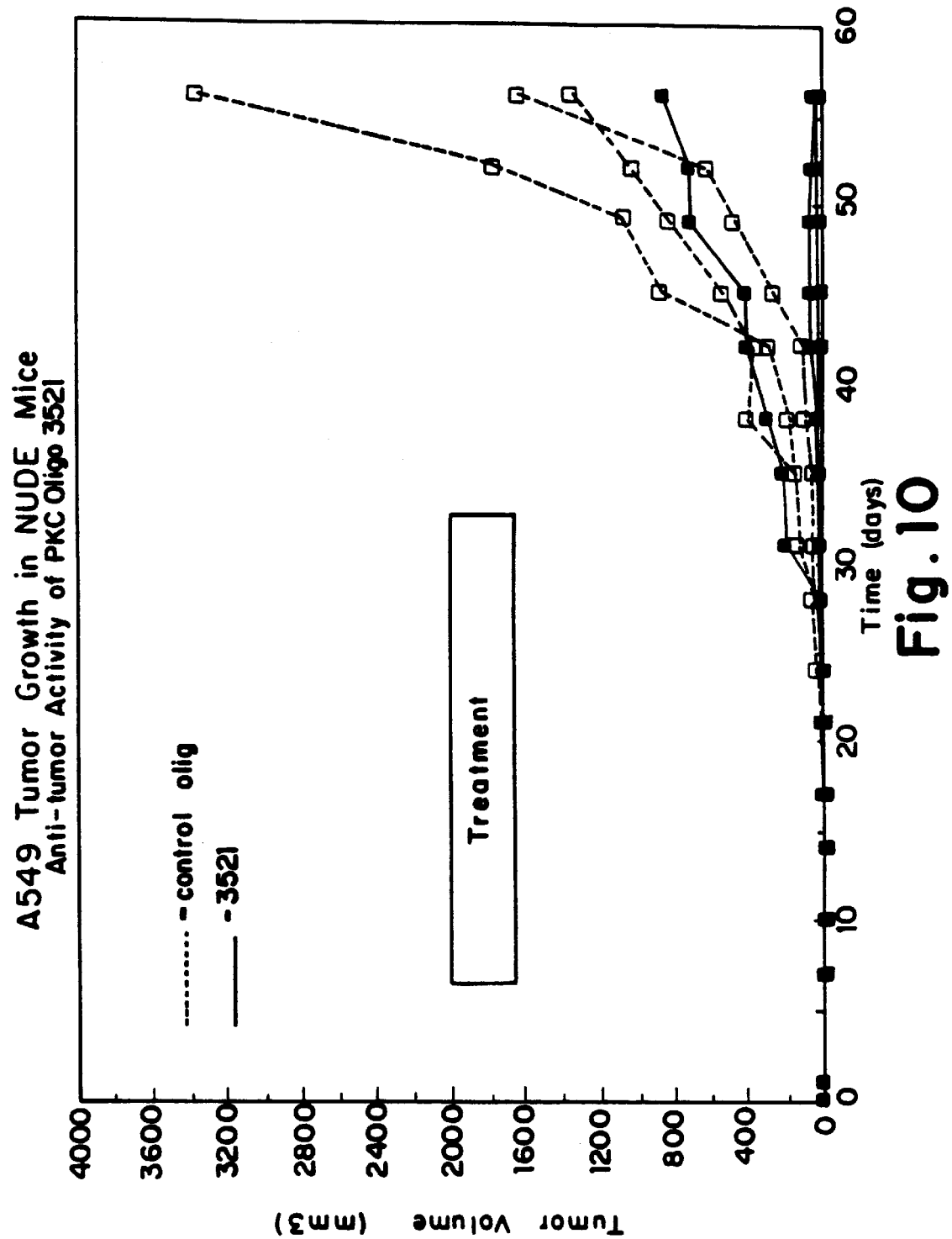

FIG. 10 is a line graph showing anti-tumor activity of ISIS 3521 (SEQ ID NO:2). Each dashed line represents tumor volume in one animal treated with control oligonucleotide; each solid line represents tumor volume in one animal treated with ISIS 3521.

Figure 11A:
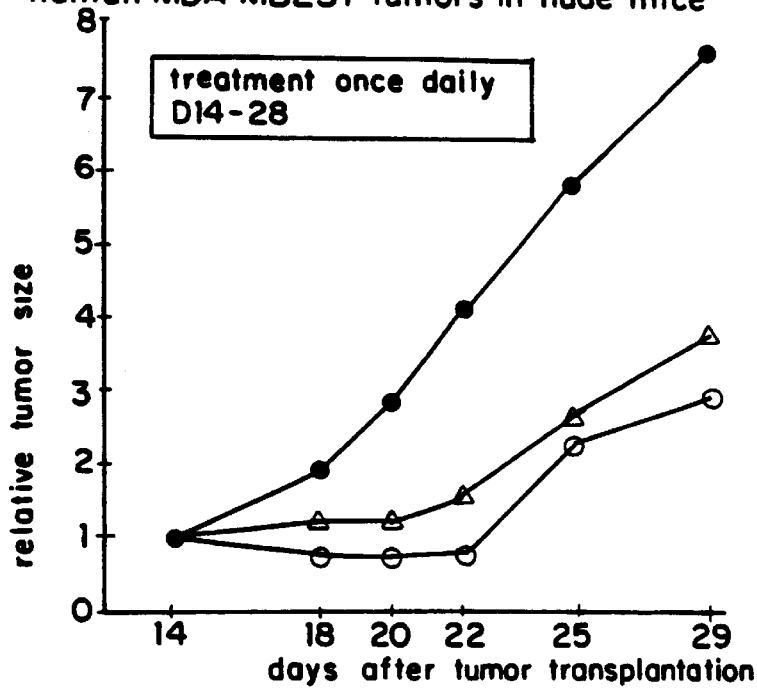
Figure 11B:
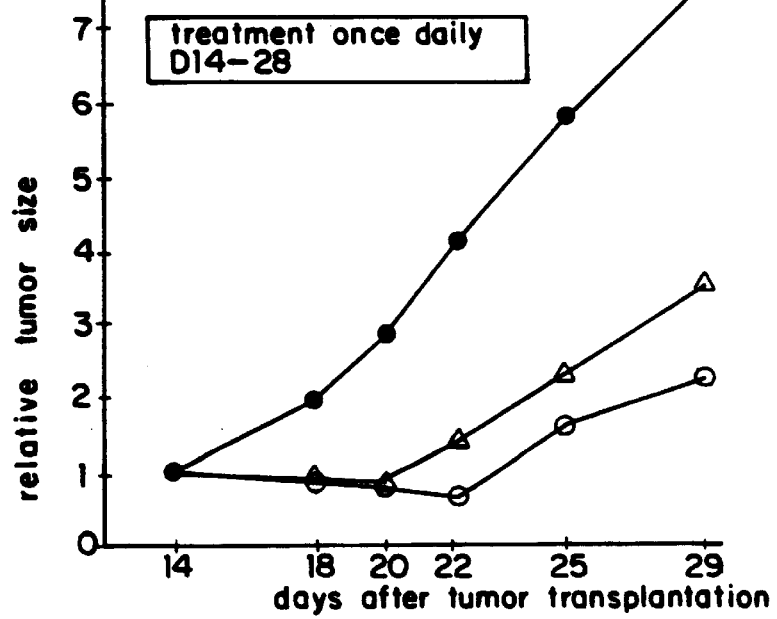

FIGS. 11A and 11B are a set of line graphs showing effect of oligonucleotides on growth of human MDA-MB231 tumors in nude mice. FIG. 11A shows results obtained with ISIS 3521 (SEQ ID NO:2); FIG. 11B shows results obtained with ISIS3527 (SEQ ID NO:5). Each line represents tumor volume in one animal. ●=control; ○=oligonucleotide at 60 mg/kg; △=oligonucleotide at 6 mg/kg.

FIG. 12 is a bar graph showing effect of 20-mer phosphorothioate oligonucleotides on PKC-η expression in A549 cells. The following oligonucleotides were used: 6432 (SEQ ID NO:43), 6433 (SEQ ID NO:44), 6443 (SEQ ID NO:42), 6431 (SEQ ID NO:40), 6442 (SEQ ID NO:41), 6441 (SEQ ID NO:46), 6435 (SEQ ID NO:45), 6436 (SEQ ID NO:54), 6434 (SEQ ID NO:55), 6444 (SEQ ID NO:56), 6445 (SEQ ID NO:57), 6446 (SEQ ID NO:58), 6553 (SEQ ID NO:59), 6581 (SEQ ID NO:47), 6605 (SEQ ID NO:60), 6580 (SEQ ID NO:48), 6579 (SEQ ID NO:61), and 6603 (SEQ ID NO:62).

FIG. 13 is a nucleotide sequence (SEQ ID NO: 104) of a portion of the 3' untranslated region of the human PKCα gene beginning at the Bcl I site near the 3' end of the previously known sequence and extending in the 3' direction. Newly determined sequences begin at nucleotide 56 and are underlined (SEQ ID NO:105). Bold sequences are unique to the long mRNA transcript of PKCα (SEQ ID NO:106).

Figure 14:
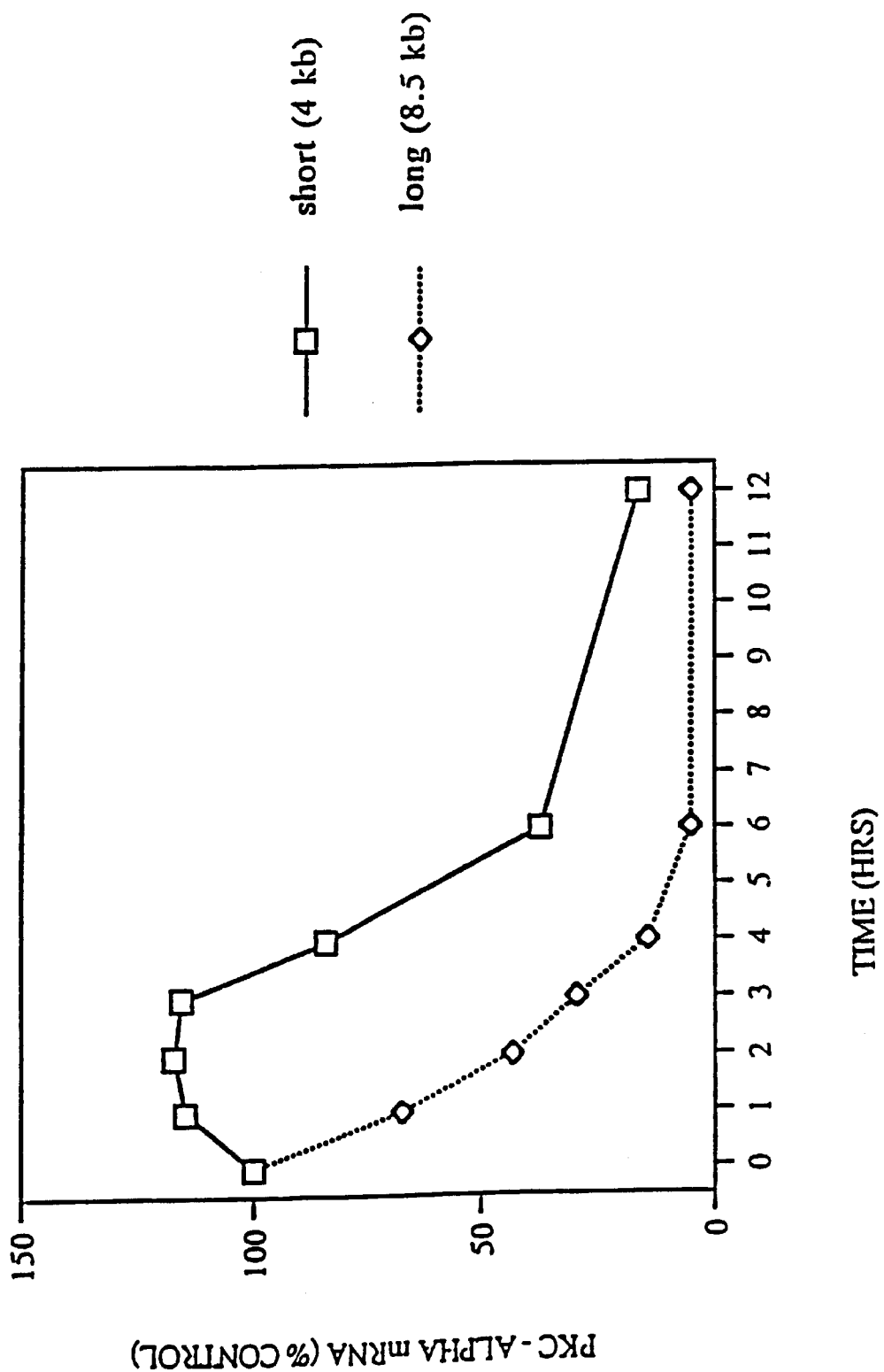

FIG. 14 is a line graph showing a time course of PKCα mRNA levels in cells (shown as percent of control) after treatment with oligonucleotide 7911 (SEQ ID NO: 117). Levels of both the short and long mRNA transcripts are indicated. Levels of short mRNA transcript are represented by solid lines. Levels of long mRNA transcript are represented by dotted lines. By 12 hours after treatment with ISIS 7911 (SEQ ID NO: 117), levels of both messages were reduced by over 80%.

SUMMARY OF THE INVENTION

In accordance with the present invention, oligonucleotides are provided that are specifically hybridizable with DNA or RNA deriving from the gene that encodes PKC. The oligonucleotide comprises nucleotide units sufficient in identity and number to effect such specific hybridization. This relationship is commonly denominated as "antisense". In one preferred embodiment, the oligonucleotides are specifically hybridizable with the translation initiation codon of the gene, and preferably comprise a sequence CAT. In another preferred embodiment, the oligonucleotides are specifically hybridizable with the 5'-untranslated or 3'-untranslated regions of the gene. In yet another preferred embodiment, oligonucleotides are provided that are specifically hybridizable with DNA or mRNA encoding a particular PKC isozyme or a particular set of PKC isozymes. Such oligonucleotides may be conveniently and desirably presented in a pharmaceutically acceptable carrier.

In accordance with other preferred embodiments, the oligonucleotides comprise one or more chemical modifications which convey some desired characteristic such as improved target affinity, cellular uptake or stability in the presence of cellular nucleases. Examples of modifications having such utility are 2'—O—alkyl and 2'-fluoro sugar modifications and phosphorothioate backbone modifications.

Other aspects of the invention are directed to methods for modulating the expression of PKC or of a particular PKC isozyme or set of isozymes in cells or tissues. Additional aspects of the invention are directed to methods of detection in cells or tissues of the DNA or RNA that encodes PKC and specific detection in cells or tissues of RNA or DNA that encodes particular PKC isozymes. Such methods comprise contacting cells or tissues suspected of containing said gene with oligonucleotides in accordance with the invention in order to interfere with the effect of or to detect said RNA or DNA.

Other aspects of the invention are directed to methods for diagnostics and therapeutics of animals suspected of having a disease associated with PKC or one of its isozymes. Such methods comprise contacting the animal or cells or tissues or a bodily fluid from the animal with oligonucleotides in accordance with the invention in order to modulate the expression of PKC, to treat conditions associated with PKC, or to effect a diagnosis thereof.

This invention provides nucleic acid sequences that encode portions of the 3' untranslated region of human PKCα. Polynucleotide probes and methods of detecting PKCα are also provided. In some embodiments of the present invention, nucleic acid sequences specific for a particular mRNA transcript of PKCα are provided, as well as polynucleotide probes and methods for specific detection of this transcript.

In accordance with other embodiments of the present invention, antisense oligonucleotides are provided that are specifically hybridizable with nucleic acids encoding PKCα. In still other embodiments, antisense oligonucleotides are provided which are specifically hybridizable with a particular mRNA transcript of PKCα. Such oligonucleotides may be conveniently and desirably presented in a pharmaceutically acceptable carrier.

In accordance with still other aspects of the invention are provided methods for modulating the expression of PKCα or of a particular PKCα mRNA transcript in cells. Additional aspects of the invention are directed to methods of detection in cells of nucleic acids that encode PKCα and specific detection in cells of nucleic acids that encode particular PKCα transcripts. Such methods comprise contacting the cells with oligonucleotides in accordance with the invention in order to interfere with the effect of or to detect said nucleic acid.

In still other embodiments of the invention are provided methods for treating animals having a disease associated with expression of PKCα or one of its transcripts. Such methods comprise contacting the animal with a therapeutically effective amount of oligonucleotides in accordance with the invention in order to modulate the expression of PKCα, to treat conditions associated with PKCα, or to effect a diagnosis thereof.

DETAILED DESCRIPTION OF THE INVENTION

Antisense oligonucleotides are now accepted as therapeutic agents having promise for the treatment of many human diseases. Oligonucleotides specifically bind (hybridize) to the complementary sequence of DNA, pre-mRNA or mature mRNA, as defined by Watson-Crick base pairing, interfering with the flow of genetic information from DNA to protein. The properties of antisense oligonucleotides which make them specific for their target sequence also make them extraordinarily versatile. Because antisense oligonucleotides are long chains of monomeric units, they may be readily synthesized for any target RNA sequence.

Numerous recent studies have documented the utility of antisense oligonucleotides as biochemical tools for studying target proteins (Rothenberg et al., *J. Natl. Cancer Inst.*, 81:1539–1544 (1989); Zon, G., *Pharmaceutical Res.*, 5:539–549 (1988). Because of recent advances in oligonucleotide chemistry and synthesis of oligonucleotides which exhibit enhanced cell uptake, target binding affinity and nuclease resistance, it is now possible to consider the use of antisense oligonucleotides as a novel form of therapeutics. For example, antisense oligonucleotides targeted to c-myb have been used to completely eliminate myeloid leukemia cells from bone marrow derived from patients with acute myelogenous leukemia. Gewirtz and Calabretta, U.S. Pat. No. 5,098,890. An antisense oligonucleotide has been shown to have clinical efficacy in humans for treatment of cytomegalovirus retinitis infections.

Antisense oligonucleotides offer an ideal solution to the problems encountered in prior art approaches to the treatment of conditions associated with PKC. They can be designed to selectively inhibit a given isozyme or particular set of isozymes, or to inhibit all members of a given family of isozymes.

Current agents which modulate the activity or metabolism of protein kinase C exhibit many unacceptable side effects due to their lack of specificity, or they exhibit only limited effectiveness in inhibiting the enzyme. The instant invention circumvents problems encountered by prior workers by modulating the production of the enzyme, rather than inhibiting the enzyme directly, to achieve the therapeutic effect. In the instant invention, the oligonucleotide is designed to hybridize directly to mRNA or to a gene, ultimately modulating the amount of PKC protein made from the gene. "Hybridization," in the context of this invention, means hydrogen bonding, also known as Watson-Crick base pairing, between complementary bases, usually on opposite nucleic acid strands or two regions of a nucleic acid strand, to form a double-stranded duplex. Guanine and cytosine are examples of complementary bases which are known to form three hydrogen bonds between them. Adenine and thymine are examples of complementary bases which are known to form two hydrogen bonds between them. "Specifically hybridizable" and "substantially complementary" are terms which indicate a sufficient degree of complementarity to avoid non-specific binding of the oligonucleotide (or polynucleotide probe) to non-target sequences under conditions in which specific binding is desired, i.e., under physiological conditions in the case of in vivo assays and therapeutic treatment, or, in the case of in vitro assays, under conditions in which the assays are conducted. It is understood that an oligonucleotide or polynucleotide probe need not be 100% complementary to its target nucleic acid sequence to be specifically hybridizable.

The relationship between an oligonucleotide and its complementary (or "target") nucleic acid is commonly denoted as "antisense."

It is preferred to target specific genes for antisense attack. It has been discovered that the genes coding for PKC α, β, γ, δ, ε, ζ and η are particularly useful for this approach. Inhibition of PKC expression is expected to be useful for the treatment of diseases, particularly hyperproliferative and inflammatory disorders.

However, "modulation" in the context of this invention means either an increase or decrease (stimulation or inhibition) of PKC expression.

In the context of this invention, the term "oligonucleotide" refers to a polynucleotide formed from naturally occurring nucleobases and pentofuranosyl (sugar) groups joined by native phosphodiester bonds. This term effectively refers to naturally occurring species or synthetic species formed from naturally occurring subunits or their close homologs.

The term "oligonucleotide" may also refer to moieties which function similarly to naturally occurring oligonucleotides but which have non-naturally occurring portions. Thus, oligonucleotides may have altered sugar moieties, nucleobases or inter-sugar ("backbone") linkages. Such modified or substituted oligonucleotides are often preferred over native forms because of properties such as, for example, enhanced cellular uptake, enhanced target binding affinity and increased stability in the presence of nucleases.

Specific examples of some preferred oligonucleotides envisioned for this invention are those which contain intersugar backbone linkages such as phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Phosphorothioates are also most preferred. Also preferred are oligonucleotides having morpholino backbone structures. Summerton, J. E. and Weller, D. D., U.S. Pat. No. 5,034,506. In other preferred embodiments, such as the peptide nucleic acid (PNA—referred to by some as "protein nucleic acid") backbone, the phosphodiester backbone of the oligonucleotide may be replaced with a polyamide backbone wherein nucleosidic bases are bound directly or indirectly to aza nitrogen atoms or methylene groups in the polyamide backbone see, e.g., P. E. Nielsen, M. Egholm, R. H. Berg, O. Buchardt, *Science* 1991, 254, 1497 and U.S. patent application Ser. No. 08/054,363, filed Apr. 26, 1993 and incorporated herein by reference. In accordance with other preferred embodiments, the phosphodiester bonds are substituted with structures which are chiral and enantiomerically specific. Persons of ordinary skill in the art will be able to select other linkages for use in practice of the invention.

Oligonucleotides may also include species which include at least one modified nucleobase. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'—O—alkyl— and 2'-halogen-substituted nucleotides. Some specific examples of modifications at the 2' position of sugar moieties which are useful in the present invention are OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $OF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

Chimeric or "gapped" oligonucleotides are also preferred embodiments of the invention. These oligonucleotides contain two or more chemically distinct regions, each comprising at least one nucleotide. Typically, one or more region comprises modified nucleotides that confer one or more beneficial properties, for example, increased nuclease resistance, increased uptake into cells or increased binding affinity for the RNA target. One or more unmodified or differently modified regions retain the ability to direct Rnase H cleavage. Chimeric oligonucleotides are disclosed in PCT application US92/11339 which is assigned to the assignee of the instant application and which is incorporated by reference herein in its entirety. Examples of chimeric oligonucleotides which are presently preferred are 2'—O—methyl or 2'—O—propyl oligonucleotides having a "deoxy gap" region of 2'-deoxynucleotides. Usually this deoxy gap region is located between the two 2'-alkyl regions. In these preferred embodiments, the internucleotide (backbone) linkages may be uniformly phosphorothioate or some combination of phosphorothioate and phosphodiester linkages.

All such oligonucleotides are best described as being functionally interchangeable with natural oligonucleotides (or synthesized oligonucleotides along natural lines), but having one or more differences from natural structure. All such oligonucleotides are comprehended by this invention so long as they function effectively to hybridize with the PKC RNA.

The oligonucleotides in accordance with this invention preferably comprise from about 5 to about 50 nucleotide units. It is more preferred that such oligonucleotides comprise from about 8 to 30 nucleotide units, and still more preferred to have from about 12 to 25 nucleotide units. As will be appreciated, a nucleotide unit is a base-sugar combination (or a combination of analogous structures) suitably bound to an adjacent nucleotide unit through phosphodiester or other bonds forming a backbone structure.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as phosphorothioates or alkylated derivatives. Other modified and substituted oligomers can be similarly synthesized.

In accordance with this invention, persons of ordinary skill in the art will understand that messenger RNA includes not only the coding region, which contains information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the coding ribonucleotides. In preferred embodiments, the oligonucleotide is specifically hybridizable with a transcription initiation site, a translation initiation site, a 5' cap region, an intron/exon junction, coding sequences or sequences in the 5'- or 3'-untranslated region.

The oligonucleotides of this invention are designed to be hybridizable with the PKC gene or with messenger RNA derived from the PKC gene. Such hybridization, when accomplished, interferes with the normal roles of the messenger RNA to cause a modulation of its function in the cell. The functions of messenger RNA to be interfered with may include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to modulate expression of the PKC gene.

The oligonucleotides of this invention can be used in diagnostics, therapeutics, prophylaxis, and as research reagents and kits. Since the oligonucleotides of this invention hybridize to the PKC gene and its mRNA, sandwich and other assays can easily be constructed to exploit this fact. Furthermore, since the oligonucleotides of this invention hybridize specifically to particular isozymes of the PKC mRNA, such assays can be devised for screening of cells and tissues for particular PKC isozymes. Such assays can be utilized for diagnosis of diseases associated with various PKC forms. Provision of means for detecting hybridization of oligonucleotide with the PKC gene can routinely be accomplished. Such provision may include enzyme conjugation, radiolabelling or any other suitable detection systems. Kits for detecting the presence or absence of PKC may also be prepared.

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotides.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention also provides a nucleic acid molecule having a sequence which encodes the 3'-untranslated region of human PKCα is provided (FIG. 13). This sequence was determined from cDNA clones prepared from human A549 cells, beginning with a clone overlapping the 3'-most end of the previously published PKCα sequence [Finkenzeller et al., *Nucl. Acids Res.* 18:2183 (1990); Genbank accession number X52479] and extending in the 3' direction. A polyadenylation site which was reached after 1080 nucleotides (nucleotide 1136 in FIG. 13); has been identified as the 3' end of the short (4 kb) mRNA transcript of PKCα. An additional 676 nucleotides of sequence in the 3' direction were determined, which sequence is unique to the long (8 kb) mRNA transcript of PKCα. The nucleic acid molecule of the present invention may preferably be comprised of deoxyribonucleic acids and may be double-stranded in some aspects of the present invention. Also in accordance with the present invention, said nucleic acid molecules are isolated. "Isolated" as the term is used herein, in meant to refer to molecules which have been purified or synthesized so as to be substantially homogeneous. The term does not exclude the possibility that certain impurities may be present in the composition, but is, instead, meant to refer to the absence of non-relevant nucleic acid sequences.

In accordance with the present invention polynucleotide probes specifically hybridizable to a portion of the 3' untranslated region of the human PKCα gene are provided. Polynucleotide probes specifically hybridizable to a portion of the long mRNA transcript of PKCα are also provided. Such probes may be used for diagnostic or research purposes to detect or quantitate the expression of PKCα. Probes may be used to specifically detect or quantitate the long transcript of PKCα. Said polynucleotide probes may range in length from about 5 to about 50 nucleotide units. In more preferred embodiments of the present invention the probes may be from about 8 to about 30 nucleotide units in length. Ideally, said probes range in length from about 12 to about 25 nucleotide units. It is recognized that since polynucleotide probes of the present invention ideally do not exceed 50 nucleotides in length, said probes may specifically hybridize to only a portion of the targeted sequence. The portion of the PKCα sequence to be targeted can be identified by one skilled in the art. Most suitably, a target sequence is chosen which is unique, thereby decreasing background noise attributable to hybridization by the probe other than to the target. By way of example, one skilled in the art would be unlikely to select a repeating sequence of adenine nucleotide units as this is a common sequence occurring in many genes. The practitioner might choose to perform a search and comparison of sequences found in a sequence depository such as Genbank in order to identify and design a useful probe. Such methods are conventionally used to identify unique sequences. These unique sequences, when used as probes, need not necessarily be crucial to the regulation of the expression of PKCα.

The following examples illustrate the present invention and are not intended to limit the same.

EXAMPLES

Example 1 Oligonucleotide Synthesis

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'—O—methyl phosphorothioate oligonucleotides were synthesized according to the procedures set forth above substituting 2'—O—methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'—O—propyl phosphorothioate oligonucleotides may be prepared by slight modifications of this procedure.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, Ph 7.0.

The oligonucleotides tested are presented in Table 1. Sequence data are from the cDNA sequence published by Finkenzeller et al., *Nucl. Acids Res.* 18:2183 (1990); Genbank accession number X52479. The sequence numbers given under the oligonucleotides are relative to the first residue to be sequenced on the cDNA, which is 28 residues upstream of the ATG start codon.

TABLE 1

| SEQ ID | Sequence | | | | | | Target | ISIS # |
|---|---|---|---|---|---|---|---|---|
| 1 | CCC 19 | CAA | CCA | CCT | CTT | GCT | CC 1 | 5' Untranslated | 3520 |
| 2 | GTT 2063 | CTC | GCT | GGT | GAG | TTT | CA 2044 | 3' Untranslated | 3521 |
| 3 | AAA 41 | ACG | TCA | GCC | ATG | GTC | CC 22 | Translation init. codon | 3522 |
| 4 | GGA 2109 | TTC | ACT | TCC | ACT | GCG | GG 2090 | 3' Untranslated | 3526 |
| 5 | GAG 2211 | ACC | CTG | AAC | AGT | TGA | TC 2192 | 3' Untranslated | 3527 |
| 6 | CCC 47 | GGG | AAA | ACG | TCA | GCC | AT 28 | Translation init codon | 3674 |
| 7 | CTG 110 | CCT | CAG | CGC | CCC | TTT | GC 91 | Internal (C1) domain | 3682 |
| 8 | AGT 193 | CGG | TGC | AGT | GGC | TGG | AG 174 | Internal (C1) domain | 3686 |
| 9 | GCA 480 | GAG | GCT | GGG | GAC | ATT | GA 461 | Internal (C1) domain | 3687 |
| 10 | GGG 2080 | CTG | GGG | AGG | TGT | TTG | TT 2061 | 3' Untranslated | 3695 |
| 11 | CAC 2098 | TGC | GGG | GAG | GGC | TGG | GG 2079 | 3' Untranslated | 3875 |

TABLE 1-continued

OLIGONUCLEOTIDES TARGETED TO HUMAN PKC-α

| SEQ ID | Sequence | Target | ISIS # |
|---|---|---|---|
| 12 | AGC CGT GGC CTT AAA ATT TT 3' 2137 | 2118 Untranslated | 3878 |
| 13 | ATT TTC AGG CCT CCA TAT GG 3' 2168 | 2149 Untranslated | 3879 |
| 14 | AAG AGA GAG ACC CTG AAC AG 3' 2217 | 2198 Untranslated | 3884 |
| 15 | GAT AAT GTT CTT GGT TGT AA 3' 2235 | 2216 Untranslated | 3885 |
| 16 | ATG GGG TGC ACA AAC TGG GG Internal 2027 | 2008 (C3) domain | 3886 |
| 17 | GTC AGC CAT GGT CCC CCC CC Translation 36 | 17 init. codon | 3890 |
| 18 | CGC CGT GGA GTC GTT GCC CG Internal 63 | 44 (V1) domain | 3891 |
| 19 | TCA AAT GGA GGC TGC CCG GC Internal 1643 | 1624 (C3) domain | 3892 |
| 20 | TGG AAT CAG ACA CAA GCC GT 3' 2151 | 2132 Untranslated | 3947 |

Example 2 Cell Culture and Treatment with Phorbol Esters and Oligonucleotides Targeted to PKC-α

PKC protein half-lives have been reported to vary from 6.7 hours to over 24 hours [Young et al., *Biochem. J.* 244:775–779 (1987); Ballester et al., *J. Biol. Chem.* 260:15194–15199 (1985)]. These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct consequence of an increased rate of proteolysis of the kinase with no apparent change in synthetic rate.

We determined that in human lung carcinoma (A549) cells, treatment with the phorbol ester 12,13-dibutyrate (PDBu), using a modification of the method of Krug et al., [Krug et al., *J. Biol. Chem.* 262:11852–11856 (1987)] lowered cellular levels of PKC-α, without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Bethesda, Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.).

Cells were treated with 500 nM PDBu (Sigma Chem. Co., St. Louis, Mo.) for 12–16 hours (overnight). Cells were then washed three times in DME at 37° C., and 1 ml DMA containing 20 µl DOTMA (Lipofectin reagent, BRL, Bethesda, Md.) was added. Oligonucleotides were added to a concentration of 1 µM and the cells were incubated for a further 4 hours at 37° C.

Cells were washed once in 3 ml DME containing 0.1 mg/ml BSA and a further 2 ml DME containing 0.1 mg/ml BSA was added. Oligonucleotides (1 µM) were added and the cells were incubated at 37° C. for 24 hours.

Cells were washed three times in phosphate-buffered saline (PBS) and cellular proteins were extracted in 120 µl sample buffer (60 mM Tris pH 6.8, 2% SDS, 10% glycerol, 10 mM dithiothreitol) and boiled for 5 minutes. Intracellular levels of PKC-α protein were determined by immunoblotting.

Example 3 Immunoblot Assay for PKC Expression

Cell extracts were electrophoresed on 10% SDS-PAGE mini-gels. The resolved proteins were transferred to Immobilon-P membrane (Millipore, Bedford Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-α (UBI, Lake Placid N.Y.) diluted to 0.2 µg/ml in TBS containing 0.2% nonfat milk. This was followed by three washes in TBS plus 0.2% nonfat milk. The membrane was then incubated for one hour with $^{125}$I-labelled goat anti-mouse secondary antibody (ICN Radiochemicals, Irvine Calif.). Membranes were then washed extensively in TBS plus 0.2% nonfat milk. Bands were visualized and quantitated using a Phosphorimager (Molecular Dynamics, Sunnyvale, Calif.). PKC-α appears as a single band with a molecular weight of 80 kD.

Figure 1A:
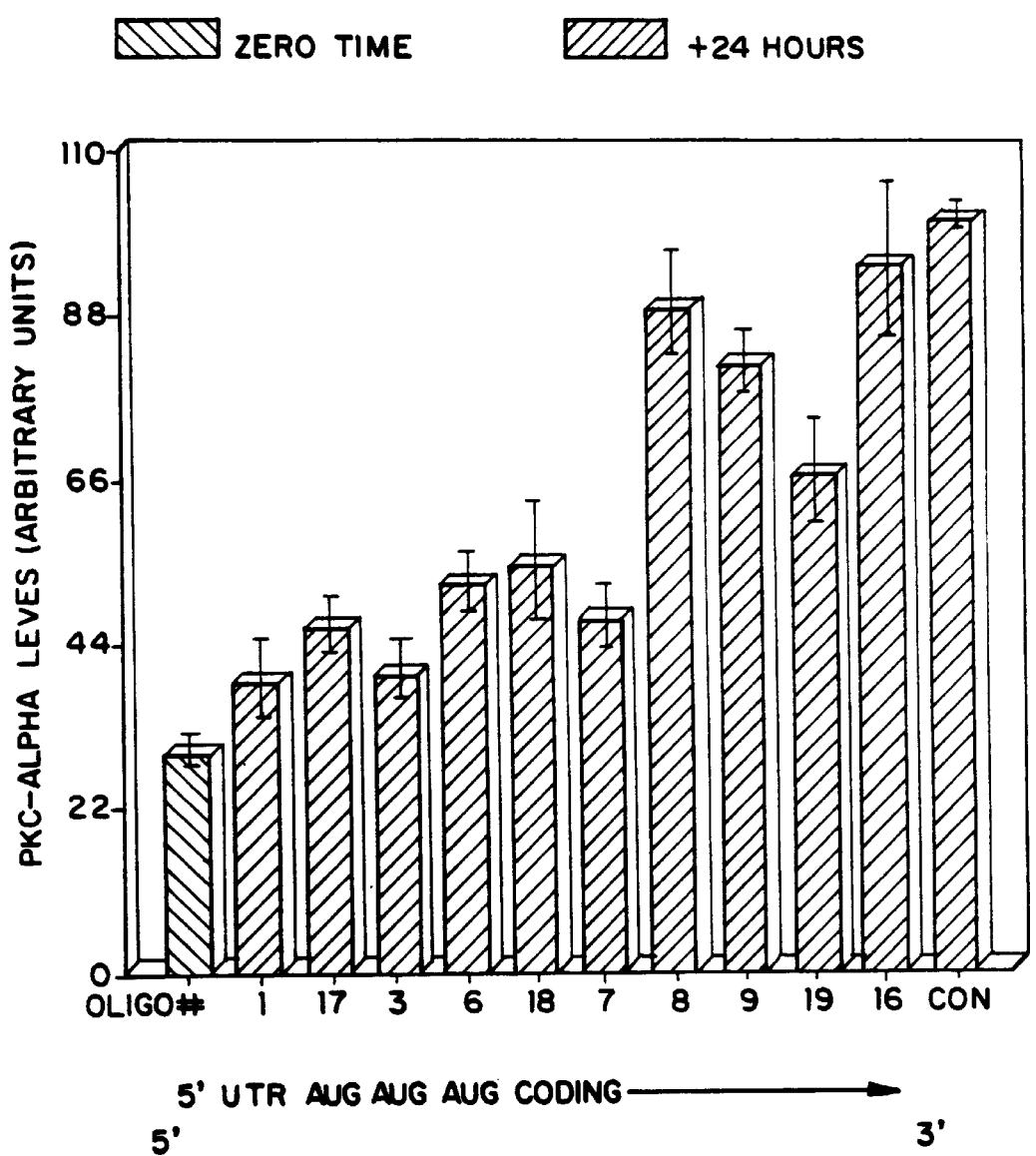
FIGS. 1(*a*) and 1(*b*) are graphical depictions of the effects on PKC expression of antisense oligonucleotides hybridizable with PKC-α. Oligonucleotides are arranged by PKC target region, 5' to 3'.
Figure 1B:
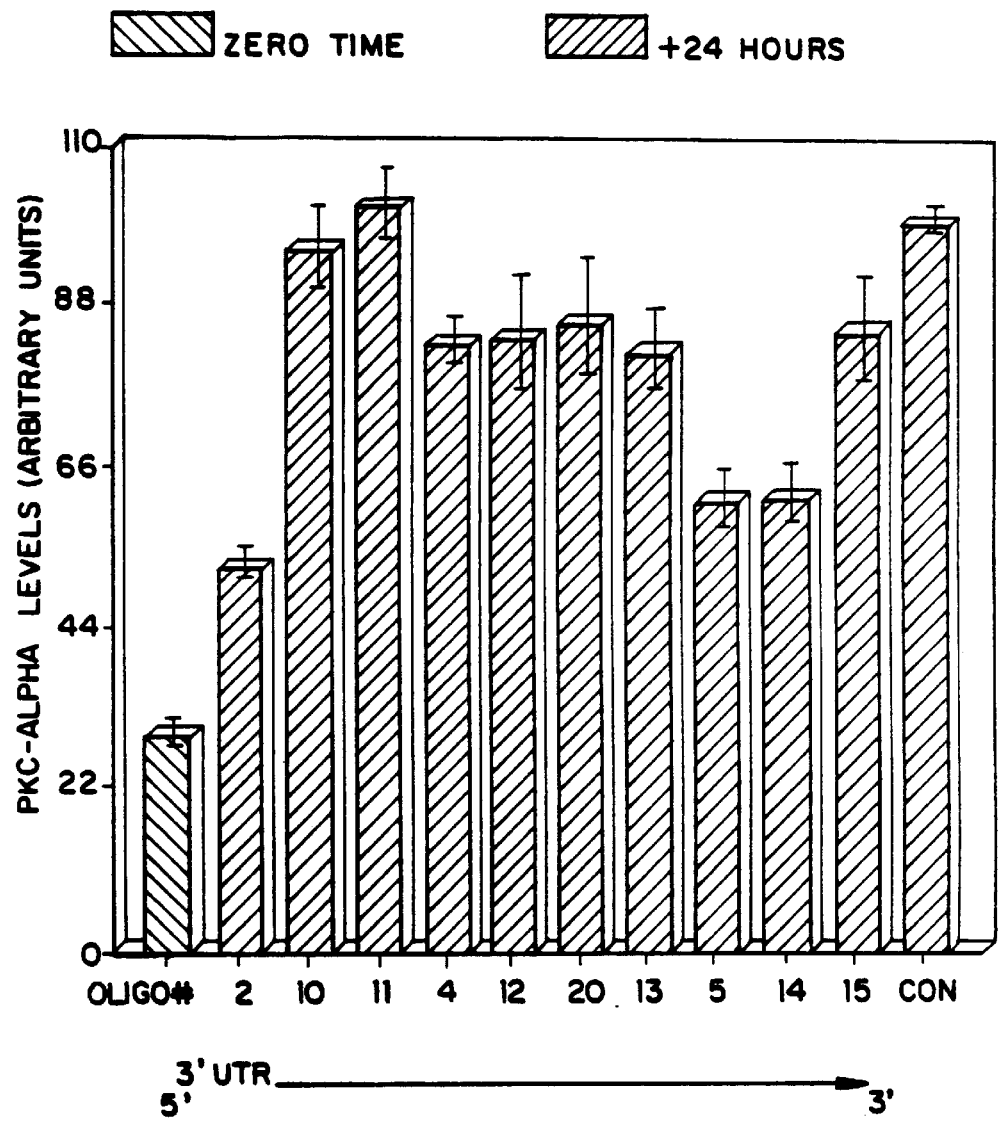

Each oligonucleotide was tested three times, in triplicate, and the results of the experiments were normalized against percentage of protein present as compared to cells which were not treated with oligonucleotide (FIGS. 1a and 1b). The five most effective oligonucleotides target the AUG start codon and regions slightly upstream and downstream from it (Sequence Nos. 1, 3, 17, 7, 6). The next most effective oligo-nucleotides are targeted toward the 3' untranslated region of the RNA (oligos 2, 5, 14).

Example 4 Other Isozymes of PKC

Results with oligonucleotides targeting human PKC-α demonstrated that the most effective target sequences were those surrounding the translation initiation codon and the 3' untranslated region. It is believed that these sequences will also be effective targets for oligo-nucleotides directed against other isozymes of PKC. Antisense oligonucleotides which are likely to be effective inhibitors of PKC are identified below. These oligonucleotides are synthesized as in Example 1, and can be screened as in Examples 2 and 3, using appropriate antibodies where available. Alternatively, a reporter gene assay system can be established, transiently co-expressing the desired isozyme of PKC with luciferase under the influence of the TPA-responsive enhancer or other suitable promoter. PKC expression is then assayed by measuring luciferase activity using standard procedures. Luciferase is extracted from cells by lysis with the detergent Triton X-100, as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY (1987). A Dynatech ML1000 luminometer is used to measure peak luminescence upon addition of luciferin (Sigma) to 625 µM.

PKC-β, Types I and II

Sequence data are from Kubo et al., *FEBS Lett.* 223: 138–142 (1987); Genbank accession numbers X06318, M27545, X07109. Sequences are numbered from the first 5' base sequenced on the cDNA. PKC-β types I and II are the result of alternative mRNA splicing of a single gene product. This results in proteins with identical amino termini (5' end of the mRNA); however, there is sequence divergence in the carboxy termini (3' end of the mRNA). The following oligonucleotides, targeted to the translation initiation codon, are expected to modulate expression of both PKC-β types I and II:

TABLE 2

OLIGONUCLEOTIDES TARGETED TO PKC-β TYPES I AND II

| SEQ ID | Sequence | Target |
|---|---|---|
| 21 | CAT CTT GCG CGC GGG GAG CC<br>139                          120 | Translation init. |
| 22 | TGC GCG CGG GGA GCC GGA GC<br>134                          115 | " |
| 23 | CGA GAG GTG CCG GCC CCG GG<br>113                           94 | " |
| 24 | CTC TCC TCG CCC TCG CTC GG<br>183                          164 | " |

The following antisense oligonucleotides are targeted to the 3'-untranslated region of PKC-β type I:

TABLE 3

OLIGONUCLEOTIDES TARGETED TO PKC-β TYPE I

| SEQ. ID | Sequence | Target |
|---|---|---|
| 25 | TGG AGT TTG CAT TCA CCT AC<br>2168                        2149 | 3' Untranslated |
| 26 | AAA GGC CTC TAA GAC AAG CT<br>2285                        2266 | " |
| 27 | GCC AGC ATG TGC ACC GTG AA<br>2250                        2231 | " |
| 28 | ACA CCC CAG GCT CAA CGA TG<br>2186                        2167 | " |
| 29 | CCG AAG CTT ACT CAC AAT TT<br>2569                        2550 | " |

The following antisense oligonucleotides are targeted to the 3'-untranslated region of PKC-β Type II:

TABLE 4

OLIGONUCLEOTIDES TARGETED TO PKC-β TYPE II

| SEQ. ID | Sequence | Target |
|---|---|---|
| 30 | ACT TAG CTC TTG ACT TCG GG<br>2160                        2141 | 3' Untranslated |
| 31 | ATG CTG CGG AAA ATA AAT TG<br>2420                        2401 | " |
| 32 | AAT TTA TTT TGA GCA TGT TC<br>2663                        2644 | " |
| 33 | TTT GGG GAT GAG GGT GAG CA<br>2843                        2824 | " |

TABLE 4-continued

OLIGONUCLEOTIDES TARGETED TO PKC-β TYPE II

| SEQ. ID | Sequence | Target |
|---|---|---|
| 34 | CCC ATT CCC ACA GGC CTG AG<br>3137                        3118 | " |

PKC-γ:

Sequence data are from Coussens et al., *Science* 233:859–866 (1986); Genbank accession number M13977. Sequences are numbered from the first 5' base sequenced in the CDNA. The full sequence is not available: the extreme 3' end of the open reading frame and the 3' untranslated region are missing. Consequently these regions are not presently available as antisense targets.

TABLE 5

OLIGONUCLEOTIDES TARGETED TO PKC-γ

| SEQ. ID | Sequence | Target |
|---|---|---|
| 35 | CGG AGC GCG CCA GGC AGG GA<br>51                            32 | 5' Untranslated |
| 36 | CCT TTT CCC AGA CCA GCC AT<br>215                          196 | Translation init. |
| 37 | GGC CCC AGA AAC GTA GCA GG<br>195                          176 | 5' of start codon |
| 38 | GGA TCC TGC CTT TCT TGG GG<br>170                          151 | 5' Untranslated |
| 39 | CAG CCA TGG CCC CAG AAA CG<br>202                          183 | Translation init. |

PKC-η:

Sequence data for PKC-η are from Bacher and colleagues [Bacher et al., *Mol. Cell. Biol.* 11:126–133 (1991)]; Genbank accession number M55284. They assign their isozyme the name PKC-L; however the sequence is almost identical to that of mouse PKC-η, so the latter nomenclature is used here for consistency. Sequences are numbered from the first 5' base sequenced in the cDNA.

TABLE 6

OLIGONUCLEOTIDES TARGETED TO PKC-η

| SEQ. ID | Sequence | Target |
|---|---|---|
| 40 | CGA CAT GCC GGC GC-<br>C GCT GC<br>172                        153 | Translation init. |
| 41 | CAG ACG ACA TGC CG-<br>G CGC CG<br>176                        157 | " |
| 42 | GCC TGC TTC GCA GCG G-<br>GA GA<br>138                        119 | " |
| 43 | ACA GGT GCA GGA GTC-<br>GAG GC<br>86                           67 | " |
| 44 | GTC CCG TCT CAG GC-<br>C AGC CC<br>111                         92 | " |

TABLE 6-continued

OLIGONUCLEOTIDES TARGETED TO PKC-η

| SEQ. ID | Sequence | Target |
|---|---|---|
| 45 | CCT CAC CGA TGC GGA C-CC TC<br>221     202 | " |
| 46 | ATT GAA CTT CAT GGT GC-C AG<br>193     174 | " |
| 47 | TCT CAC TCC CCA TAA G-GC TA<br>2046     2027 | 3' Untranslated |
| 48 | TTC CTT TGG GTT CTC GT-G CC<br>2067     2048 | " |
| 49 | TTC CAT CCT TCG ACA-GAG TT<br>2353     2336 | " |
| 50 | AGG CTG ATG CTG GGA AG-G TC<br>2300     2281 | " |
| 51 | GTT CTA AGG CTG AT-G CTG GG<br>2306     2287 | " |

Figure 2:
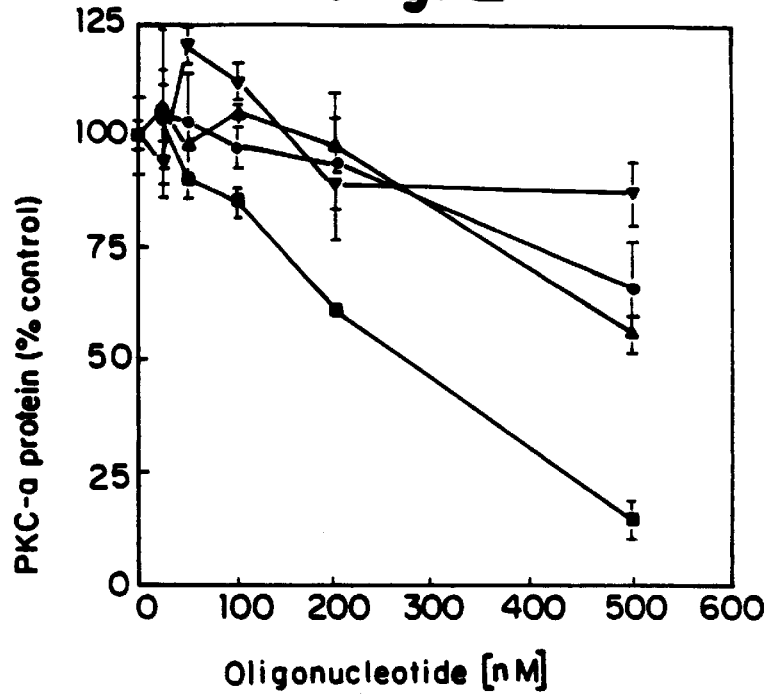
FIG. 2 is a line graph showing dose-dependent reduction of PKC-α protein levels after oligonucleotide treatment of A549 cells. ♥=ISIS 4632 CCCCAACCACCTCTTGCTCC; SEQ ID NO:120; ■=ISIS 4649 SEQ ID NO:3; ●=ISIS 4636 GTTCTCGCTGGTGAGTTTCA; SEQ ID NO:121; ▲=ISIS 4648 GAGACCCTGACCAGTTGATC; SEQ ID NO:122.

Example 5 Dose Response of Phosphorothioate/ 2'—O—Methyl Oligonucleotide Effects on PKC-α Protein Synthesis A series of phosphorothioate, fully 2'—O—methyl oligonucleotides having SEQ ID NO: 1, 2, 3 and 5 were synthesized. A549 cells were treated with 500 nM PDBu for 18 hours to downregulate PKC-α synthesis, washed to remove PDBu and then treated with oligonucleotide and DOTMA/DOPE cationic liposomes. Medium was replaced after four hours and the cells were allowed to recover for another 20 hours. Proteins were extracted and PKC-α protein levels were determined by immunoblotting as described in Example 3. Results were quantified with a phosphorimager (Molecular Dynamics, Sunnyvale Calif.) and are shown in FIG. 2 expressed as percent of control (saline treatment). ISIS 4649 (SEQ ID NO: 3; squares) reduced PKC-α protein levels by 85–90% at 500 nM and had an IC50 of approximately 260 nM.

Example 6 Effect of Antisense Oligonucleotides on PKC-α mRNA Levels

Figure 3:
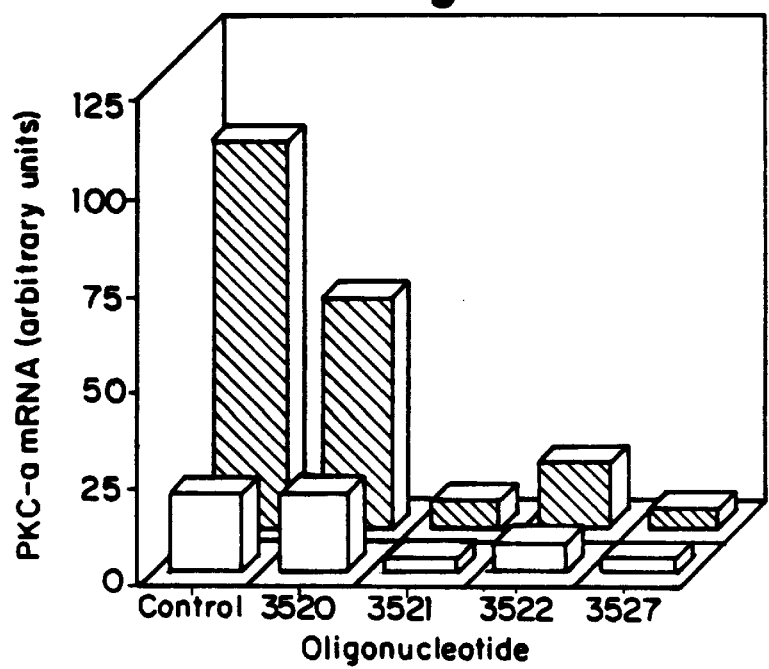
FIG. 3 is a bar graph showing reduction of PKC-α MRNA after treatment of A549 cells with oligonucleotides. Hatched bars represent the 8.5 kb transcript, plain bars represent the 4.0 kb transcript. The following oligonucleotides were used: ISIS-3520 (SEQ ID NO:1), ISIS-3521 (SEQ ID NO:2), ISIS-3522 (SEQ ID NO:3), and ISIS-3527 (SEQ ID NO:5).

A549 cells were treated with phosphorothioate oligonucleotides at 500 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$P radiolabeled PKC-α cDNA probe and then stripped and reprobed with a radiolabeled G3PDH probe to confirm equal RNA loading. Each oligonucleotide (3520, 3521, 3522 and 3527) was used in duplicate. The two major PKC-α transcripts (8.5 kb and 4.0 kb) were examined and quantified with a PhosphorImager (Molecular Dynamics, Sunnyvale Calif.). Results are shown in FIG. 3. Oligonucleotides 3521 (SEQ ID NO: 2), 3522 (SEQ ID NO: 3) and 3527 (SEQ ID NO: 5) gave better than 50% reduction of PKC-α mRNA levels. Oligonucleotides 3521 and 3527 gave approximately 80% reduction of the smaller transcript and over 90% reduction of the larger transcript.

Example 7 Chimeric (Deoxy Gapped) 2'—O—Methyl Oligonucleotides

Figure 4:
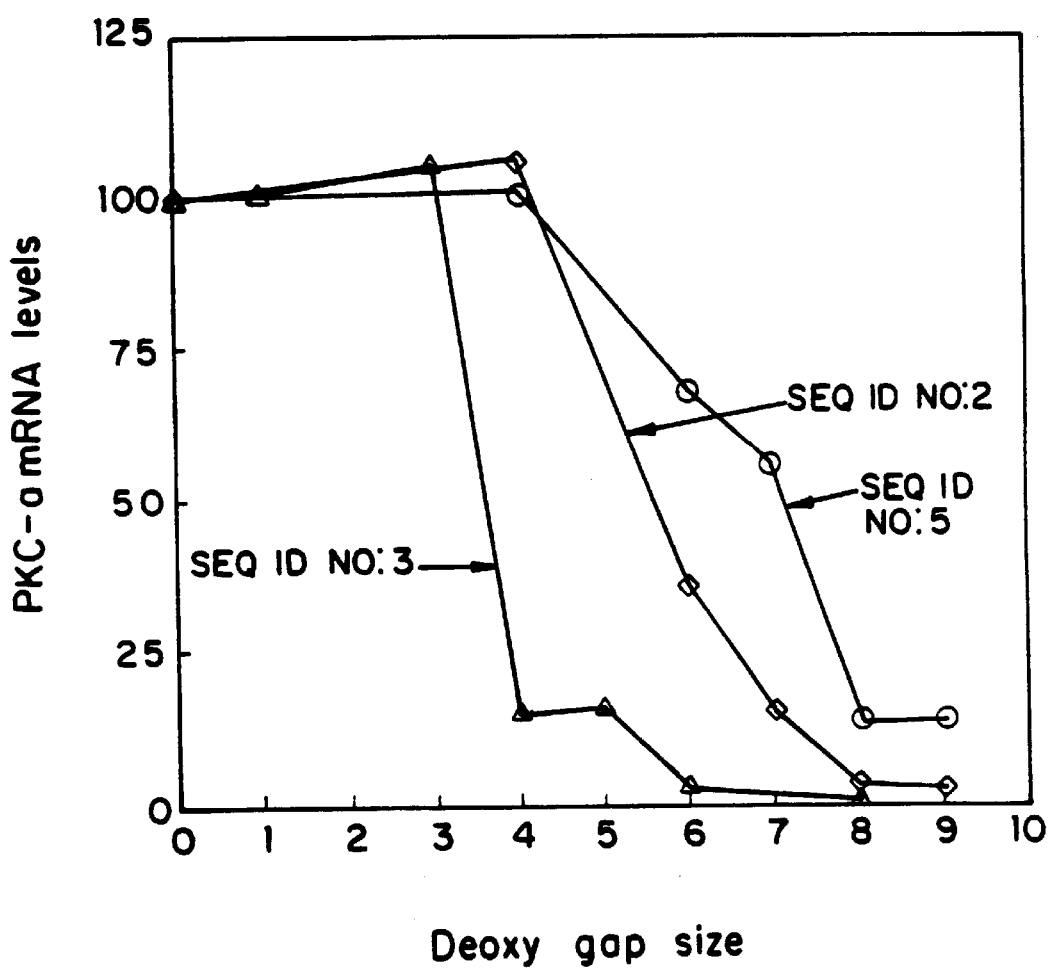
FIG. 4 is a line graph showing the relationship between deoxy gap length and activity of chimeric oligonucleotides against PKC.

Oligonucleotides 3521 (SEQ ID NO: 2), 3522 (SEQ ID NO: 3) and 3527 (SEQ ID NO: 5) were chosen for further study and modification. Oligonucleotides having these sequences were synthesized as uniformly phosphorothioate chimeric oligonucleotides having a centered deoxy gap of various lengths flanked by 2'—O—methylated regions. These oligonucleotides (500 nM concentration) were tested for effects on PKC-α mRNA levels by Northern blot analysis. Results are shown in FIG. 4. Deoxy gaps of eight nucleotides or more gave maximal reduction of PKC-α mRNA levels (both transcripts) in all cases. The oligonucleotide having SEQ ID NO: 3 reduced PKC-α mRNA by approximately 83% with a deoxy gap length of four nucleotides, and gave nearly complete reduction of PKC-α mRNA with a deoxy gap length of six or more.

Figure 5:
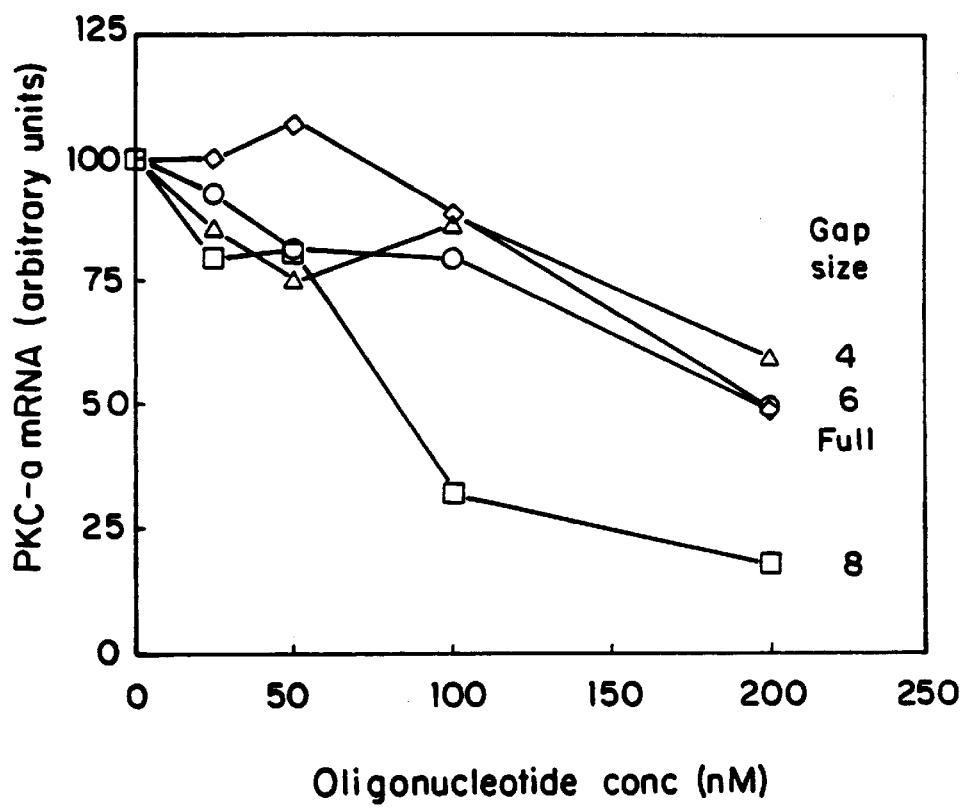
FIG. 5 is a line graph showing dose response curves for chimeric oligonucleotides (all SEQ ID NO: 3) with different deoxy gap lengths.

Dose-response curves for these oligonucleotides are shown in FIG. 5. The 2'—O—methyl chimeric oligonucleotides with four- or six-nucleotide deoxy gaps have an IC50 for PKC-α mRNA reduction (concentration of oligonucleotide needed to give a 50% reduction in PKC-α mRNA levels) of 200–250 nM, as did the full-deoxy oligonucleotide (all are phosphorothioates throughout). The 2'—O—methyl chimeric oligonucleotide with an 8-nucleotide deoxy gap had an IC50 of approximately 85 nM.

Several variations of this chimeric oligonucleotide (SEQ. ID NO: 3) were compared for ability to lower PKC-α mRNA levels. These oligonucleotides are shown in Table 7.

TABLE 7

Chimeric 2'-O-methyl/deoxy P=S oligonucleotides
bold = 2'-O-methyl; s = P=S linkage,
o = P=O linkage

| OLIGO # | SEQUENCE | SEQ ID NO: |
|---|---|---|
| 3522 | AsAsAsAsCsGsTsCsAsGsCsCsAsTsGsGsTsCsCsC | 3 |
| 5352 | AsAsAsAsCsGsTsCsAsGsCsCsAsTsGsGsTsCsCsC | 3 |
| 6996 | AoAoAoAoCoGsTsCsAsGsCsCsAsTsGoGoToCoCoC | 3 |
| 7008 | AsAoAoAoCoGsTsCsAsGsCsCsAsTsGoGoToCoCsC | 3 |
| 7024 | AsAoAoAoCoGsToCsAoGsCoCsAsTsGoGoToCoCsC | 3 |

Figure 6:
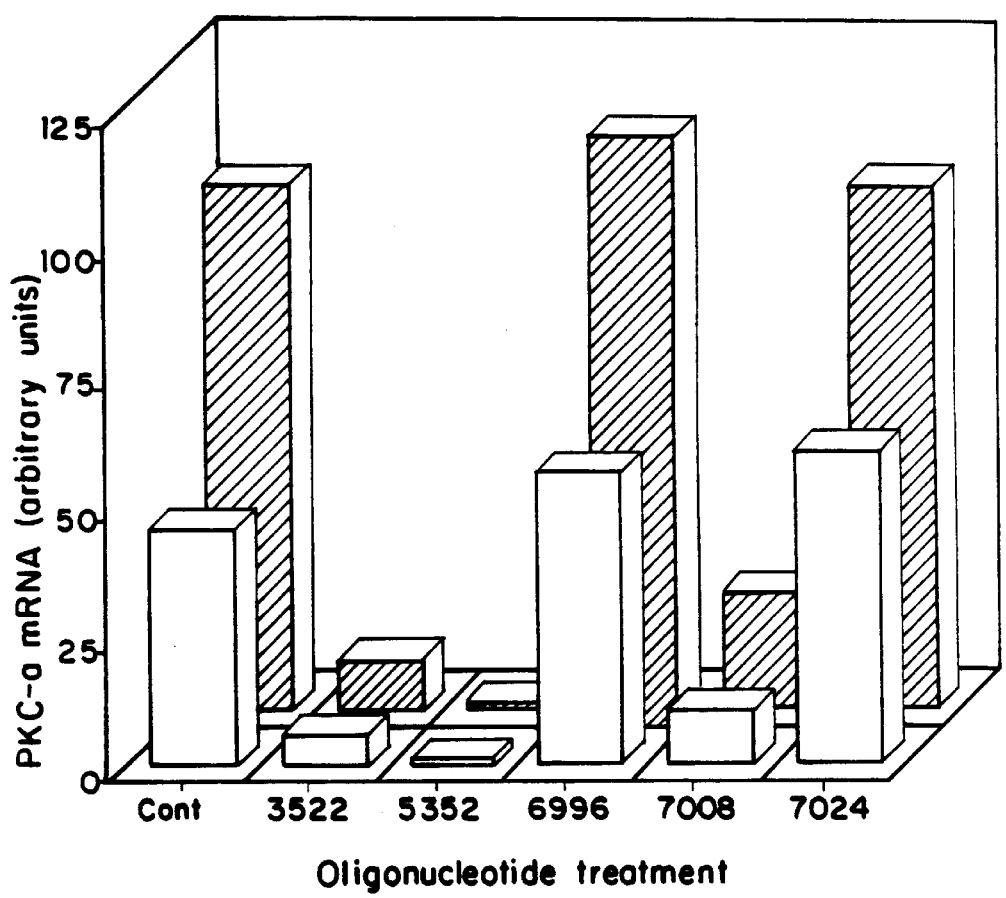
FIG. 6 is a bar graph showing the effects of several 2'—O—methyl chimeric oligonucleotides of SEQ ID NO: 3 on PKC-α mRNA levels. Hatched bars represent the 8.5 kb transcript, plain bars represent the 4.0 kb transcript.

Effects of these oligonucleotides on PKC-α mRNA levels is shown in FIG. 6. Oligonucleotides 7008, 3522 and 5352 show reduction of PKC-α mRNA, with 5352 being most active.

A series of 2'—O—propyl chimeric oligonucleotides was synthesized having SEQ ID NO: 3. These oligonucleotides are shown in Table 8.

TABLE 8

Chimeric 2'-O-propyl/deoxy P=S oligonucleotides
bold = 2+-O-propyl; s = P=S linkage,
o = P=O linkage

| OLIGO # | SEQUENCE | SEQ ID NO: |
|---|---|---|
| 7199 | AsAsAsAsCsGsTsCsAsGsCsCsAsTsGsGsTsCsC | 3 |
| 7273 | AoAoAoAoCoGsTsCsAsGsCsCsAsTsGoGoToCoCoC | 3 |
| 7294 | AsAoAoAoCoGsTsCsAsGsCsCsAsTsGoGoToCoCsC | 3 |
| 7295 | AsAoAoAoCoGsToCsAoGsCoCsAsTsGoGoToCoCsC | 3 |

Figure 7:
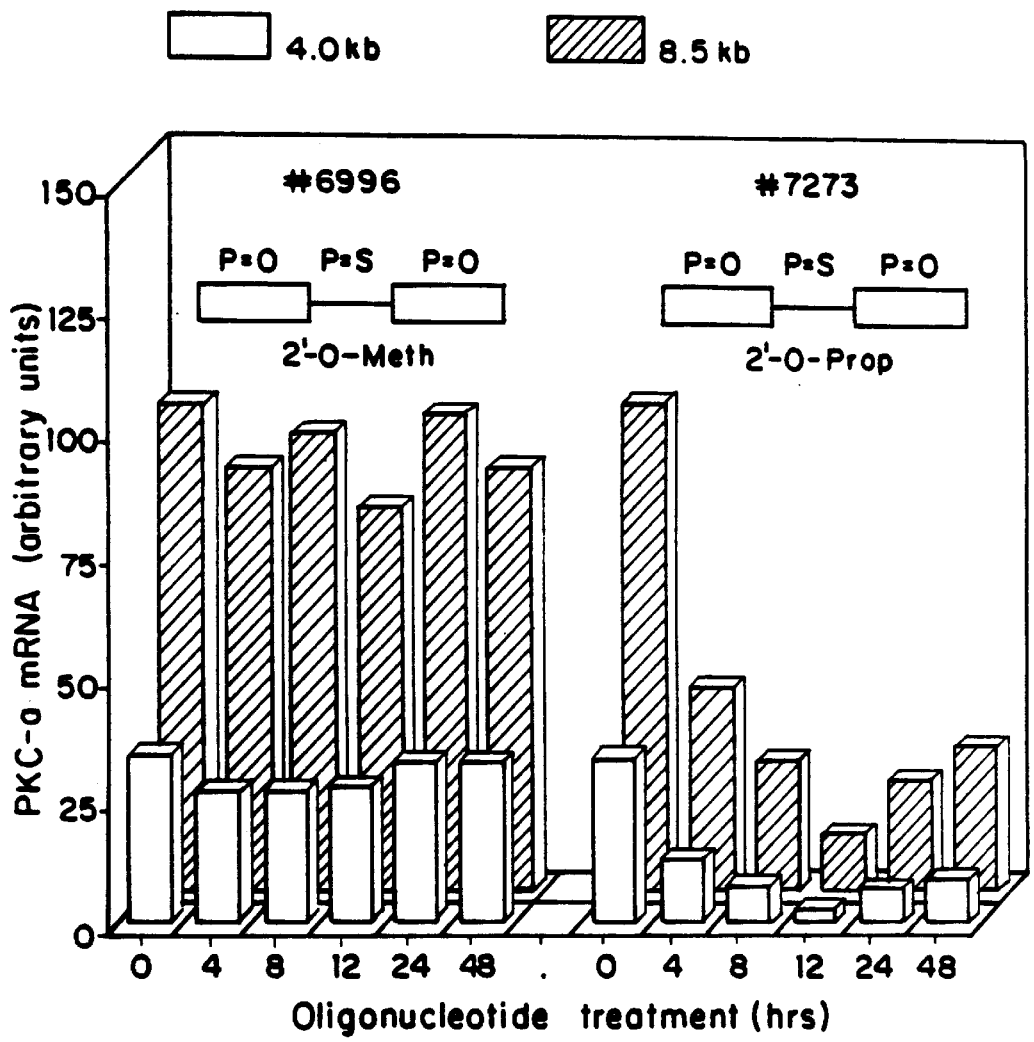
FIG. 7 is a bar graph and diagram showing the effects of several 2'—O—methyl and 2'—O—propyl chimeric oligonucleotides (6996, 7273) of SEQ ID NO: 3 on PKC-α mRNA levels. Hatched bars represent the 8.5 kb transcript, plain bars represent the 4.0 kb transcript.
Figure 8:
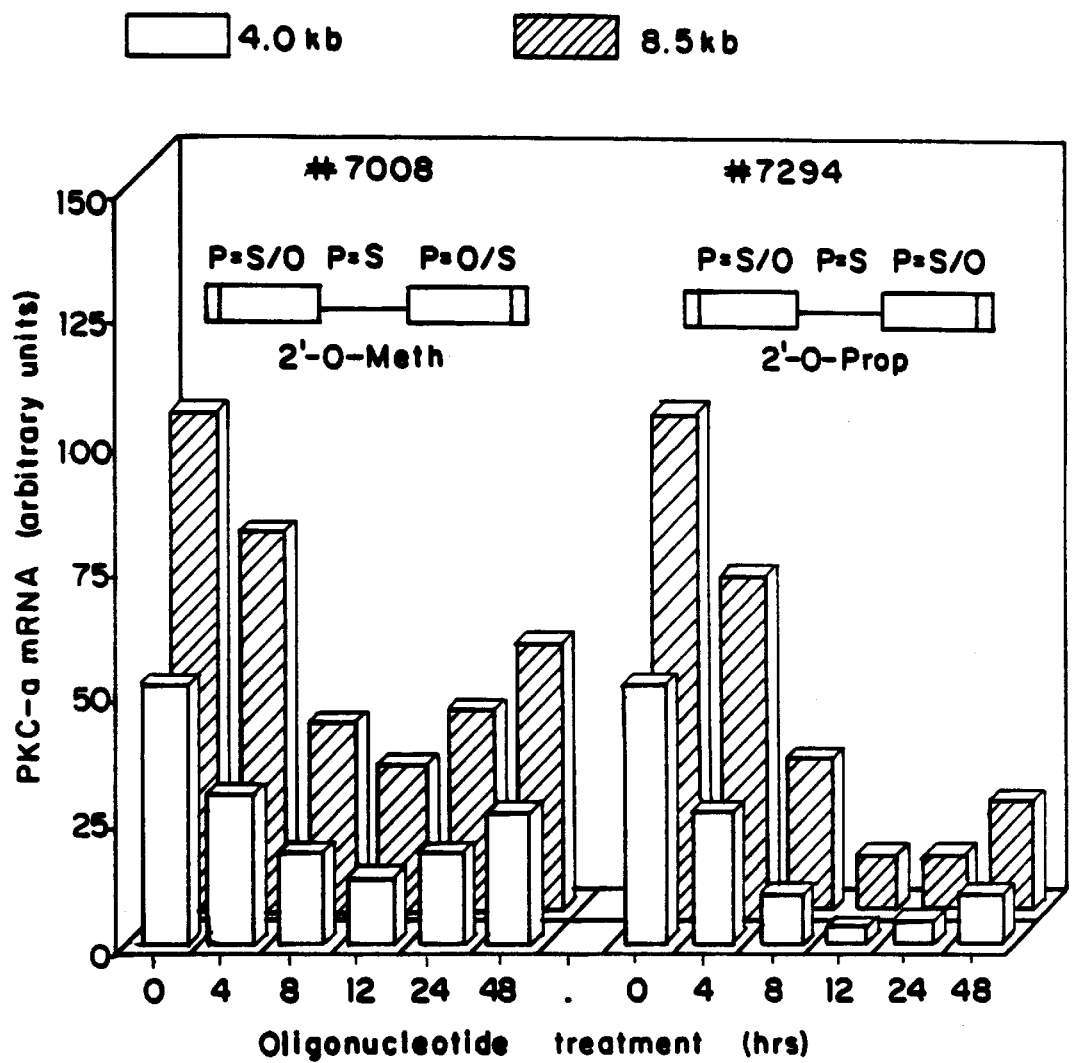
FIG. 8 is a bar graph and diagram showing the effects of additional 2'—O—methyl and 2'—O—propyl chimeric oligonucleotides (7008, 7294) of SEQ ID NO: 3 on PKC-α mRNA levels. Hatched bars represent the 8.5 kb transcript, plain bars represent the 4.0 kb transcript.

These 2'—O—propyl chimeric oligonucleotides were compared to the 2'—O—methyl chimeric oligonucleotides. Oligonucleotides 7273 and 7294 were more active than their 2'—O—methyl counterparts at lowering PKC-α mRNA levels. This is shown in FIGS. 7 and 8.

Example 8 Additional Oligonucleotides which Decrease PKC-α mRNA:

Additional phosphorothioate oligonucleotides targeted to the human PKC-α 3' untranslated region were designed and synthesized. These sequences are shown in Table 9.

TABLE 9

Chimeric 2'-O-propyl/deoxy P=S oligonucleotides
targeted to PKC-α 3'-UTR
bold = 2'-O-propyl; s = P=S linkage, o = P=O linkage

| OLIGO # | SEQUENCE | SEQ ID NO: |
|---|---|---|
| 6632 | TsTsCs TsCsGs CsTsGs GsTsGs AsGsTs TsTsC | 52 |
| 6653 | TsTsCs TsCsGs CsTsGs GsTsGs AsGsTs TsTsC | 52 |
| 6665 | ToToCo TsCsGs CsTsGs GsTsGs AsGsTo ToToC | 52 |
| 7082 | TsCsTs CsGsCs TsGsGs TsGsAs GsTsTs TsC | 53 |
| 7083 | TsCsTs CsGsCs TsGsGs TsGsAs GsTsTs TsC | 53 |
| 7084 | ToCoTo CsGsCs TsGsGs TsGsAs GsToTo ToC | 53 |

As shown in FIG. 9, oligonucleotides 6632, 6653, 7082 and 7083 are most active in reducing PKC-α mRNA levels.

Example 9 Culture of Human A549 Lung Tumor Cells

The human lung carcinoma cell line A549 was obtained from the American Type Culture Collection (Bethesda, Md.). Cells were grown in Dulbecco's Modified Eagle's Medium (Irvine Scientific, Irvine Calif.) containing 1 gm glucose/liter and 10% fetal calf serum (Irvine Scientific). Cells were trypsinized and washed and resuspended in the same medium for introduction into mice.

Example 10 Effect of ISIS 3521 on the Growth of Human A549 Tumor Cells in Nude Mice 200 μl of A549 cells (5×10$^6$ cells) were implanted subcutaneously in the inner thigh of nude mice. ISIS 3521, a phosphorothioate oligonucleotide with Sequence ID NO 2 was administered twice weekly for four weeks, beginning one week following tumor cell inoculation. Oligonucle-otides were formulated with cationic lipids (DMRIE/DOPE) and given subcutaneously in the vicinity of the tumor. Oligonucleotide dosage was 5 mg/kg with 60 mg/kg cationic lipid. Tumor size was recorded weekly.

As shown in FIG. 10, tumor growth was almost completely inhibited in two of the three mice, and reduced compared to control in the third mouse. This inhibition of tumor growth by ISIS 3521 is statistically significant. The control oligonucleotide (ISIS 1082) is a 21-mer phosphorothioate oligonucleotide without significant sequence homology to the PKC mRNA target.

Administration of oligonucleotides to mice whose tumors had already reached detectable size had no discernable effect on subsequent tumor growth.

Example 11 Effect of Antisense Oligonucleotides on Growth of Human MDA-MB231 Tumors in Nude Mice MDA-MB231 human breast carcinoma cells were obtained from the American Type Culture Collection (Bethesda, Md.). Serially transplanted MDA-MB231 tumors were established subcutaneously in nude mice. Beginning two weeks later, oligonucleotides 3521 and 3527, a phosphorothioate oligonucleotide having Sequence ID NO. 5, in saline, were administered intravenously daily for 14 days at dosages of 60 mg/kg and 6 mg/kg. Control oligonucleotide ISIS 1082 was also administered at these doses, and a saline control was also given. Tumor growth rates wre monitored for the two-week period of oligonucleotide administration. As shown in FIG. 11, both PKC-α oligonucleotides (3521 and 3527) significantly inhibit tumor growth at dosages of 60 mg/kg and 6 mg/kg. The control oligonucleotide (ISIS 1082) also showed some reduction in tumor growth, but this effect was less than with antisense oligonucleotides even at high doses, and considerably less at the lower dose. A lower-dose study was conducted using the same oligonucleotides at 6 mg/kg and 0.6 mg/kg. At 0.6 mg/kg ISIS 3521 significantly reduced tumor growth. At this concentration, ISIS 3527 also reduced tumor growth, but this result was not statistically—significant.

Example 12 Effect of Oligonucleotides on the Growth of Murine Lewis Lung Carcinoma in Mice Serially transplanted murine Lewis lung carcinomas were established in mice. Oligonucleotides 3521 and 3527 were administered intravenously every day for 14 days at doses of 6 mg/kg and 0.6 mg/kg. Tumor growth rates were monitored for the two-week period of oligonucleotide administration. As expected, these oligonucleotides, which are targeted to human PKC sequences, had insignificant effects on the mouse-derived tumors.

Example 13 Effects of Antisense Oligonucleotide ISIS 4189 on Endogenous PKC-α Expression in Hairless Mice In order to study oligonucleotide effects on endogenous PKC mRNA levels in normal animals, it was necessary to employ an oligonucleotide complementary to the murine PKC-α. ISIS 4189 is a 20-mer phosphorothioate oligonucleotide targeted to the AUG codon of mouse PKC-α. This region is without homology to the human PKC sequence and the oligonucleotide has no effect on expression of PKC-α in human cells. ISIS 4189 has an IC50 of 200 nM for mRNA reduction in C127 mouse breast epithelial cells. ISIS 4189 in saline was administered intraperitoneally to hairless mice at concentrations of 1, 10 or 100 mg/kg body weight. Injections were given daily for seven days. Tissues from liver, kidney, spleen, lung and skin were removed and PKC-α mRNA and protein levels were determined. Histopathological examination was also performed on liver, kidney and lung samples. ISIS 4189 at 100 mg/kg inhibited endogenous PKC-α mRNA levels in the mouse liver to 10–15% of control (saline) levels.

Example 14 Screening of Antisense Oligonucleotides Complementary to Human PKC-η

A series of 20-mer phosphorothioate oligonucleotides complementary to human PKC-η were synthesized. These oligonucleotides were screened at a concentration of 500 nM for ability to decrease PKC-η mRNA levels in human A549 cells, using a Northern blot assay. The oligonucleotide sequences are shown in Table 10 and the results are shown in FIG. 12.

TABLE 10

OLIGONUCLEOTIDES TARGETED TO HUMAN PKC-η mRNA

| ISIS# | Sequence | Target | SEQ ID NO: |
|---|---|---|---|
| 6431 | CGA CAT GCC GGC GCC GCT GC | AUG | 40 |
| 6442 | CAG ACG ACA TGC CGG CGC CG | AUG | 41 |
| 6443 | GCC TGC TTC GCA GCG GGA GA | 5' UTR | 42 |
| 6432 | ACA GGT GCA GGA GTC GAG GC | 5' UTR | 43 |
| 6433 | GTC CCG TCT CAG GCC AGC CC | 5' UTR | 44 |
| 6435 | CCT CAC CGA TGC GGA CCC TC | Coding | 45 |
| 6441 | ATT GAA CTT CAT GGT GCC AG | Coding | 46 |
| 6581 | TCT CAC TCC CCA TAA GGC TA | 3' UTR | 47 |
| 6580 | TTC CTT TGG GTT CTC GTG CC | 3' UTR | 48 |
| 6436 | AAC TCG AGG TGG CCG CCG TC | Coding | 54 |
| 6434 | CGC CTT CGC ATA GCC CTT TG | Coding | 55 |
| 6444 | GGA AGG GGT GAT TGC GGG CC | Coding | 56 |
| 6445 | AAC ACG CCC ATT GCC CAC CA | Coding | 57 |
| 6446 | GTC TCA AGA TGG CGT GCT CG | Coding | 58 |

TABLE 10-continued

OLIGONUCLEOTIDES TARGETED TO HUMAN PKC-η mRNA

| ISIS# | Sequence | Target | SEQ ID NO: |
|---|---|---|---|
| 6553 | GCG ATG GTT CAG CTG GGC GG | Coding | 59 |
| 6605 | GCC CTC TCT CTC ACT CCC CA | 3' UTR | 60 |
| 6579 | CTG GGA AGG TCC GAT AGA GG | 3' UTR | 61 |
| 6603 | AAG GCT GAT GCT GGG AAG GT | 3' UTR | 62 |

Oligonucleotides 6432, 6443, 6431, 6442, 6435, 6434, 6445, 6553, 6581 and 6603 reduced PKC-η mRNA levels by greater than 50%. The most potent oligonucleotides were ISIS 6581 (targeting 3' untranslated region) and ISIS 6445 (targeting coding region) which gave nearly complete loss of PKC mRNA in this assay.

Example 15 Screening of Antisense Oligonucleotides Complementary to Human PKC-ζ

A series of 20-mer phosphorothioate oligonucleotides complementary to human PKC-ζ were synthesized as described in Example 1. The source of the target sequence was Genbank locus HSPKCZ, accession number Z15108 (Hug, H.). These oligonucleotides were screened at a concentration of 500 nM for ability to decrease PKC-ζ mRNA levels in human A549 cells, substantially as described in Example 6 using a Northern blot assay. The oligonucleotide sequences and results of the screen are shown in Table 11.

TABLE 11

INHIBITION OF mRNA EXPRESSION IN HUMAN A549 CELLS USING ANTISENSE OLIGONUCLEOTIDES COMPLEMENTARY TO PKC-Z

| Oligo # | Sequence | Target region | % Inhib. | Seq. ID |
|---|---|---|---|---|
| 9007 | CGCCGCTCCCTTCCATCTTG | AUG | 70 | 63 |
| 9008 | CCCCGTAATGCGCCTTGAGG | Coding | 68 | 64 |
| 9009 | CTGTCCACCCACTTGAGGGT | Coding | 19 | 65 |
| 9010 | GCTTCCTCCATCTTCTGGCT | Coding | 35 | 66 |
| 9011 | CGGTACAGCTTCCTCCATCT | Coding | 58 | 67 |
| 9012 | TTGGAAGAGGTGGCCGTTGG | Coding | 80 | 68 |
| 9013 | CCTGTTAAAGCGCTTGGCTT | Coding | 71 | 69 |
| 9014 | TGCAGGTCAGCGGGACGAGG | Coding | 41 | 70 |
| 9015 | GCTCTTGGGAAGGCATGACA | Coding | 59 | 71 |
| 9016 | TTCTTCAACCGCACCAGGAG | Coding | 0 | 72 |
| 9017 | TTCTTCAACCGCACCAGGAG | Coding | 73 | 73 |
| 9018 | CTCTGCCTCTGCATGTGGAA | Coding | 63 | 74 |
| 9019 | TCCTTGCACATGCCGTAGTC | Coding | 31 | 75 |
| 9020 | TCCACGCTGAACCCGTACTC | Coding | 80 | 76 |
| 9021 | GGAGCGCCCGGCCATCATCT | Coding | 81 | 77 |

TABLE 11-continued

INHIBITION OF mRNA EXPRESSION IN HUMAN A549 CELLS USING ANTISENSE OLIGONUCLEOTIDES COMPLEMENTARY TO PKC-Z

| Oligo # | Sequence | Target region | % Inhib. | Seq. ID |
|---|---|---|---|---|
| 9022 | GGGCTCGCTGGTGAACTGTG | Coding | 83 | 78 |
| 9023 | GACGCACGCGGCCTCACACC | Stop | 82 | 79 |
| 9024 | GGGTCAATCACGCGTGTCCA | 3' UTR | 70 | 80 |
| 9025 | TCGGAGCCGTGCCCAGCCTG | 3' UTR | 82 | 81 |
| 9026 | CGGGCCAGGTGTGAGGGACT | 3' UTR | 40 | 82 |
| 9027 | CCGCGACGCAGGCACAGCAG | 3' UTR | 38 | 83 |
| 9028 | TGGAAACCGCATGACAGCCC | 3' UTR | 54 | 84 |
| 9029 | GGTCAGTGCATCGAGTTCTG | 3' UTR | 79 | 85 |

In this experiment, oligonucleotides 9007, 9008, 9011, 9012, 9013, 9015, 9017, 9018, 9020, 9021, 9022, 9023, 9024, 9025, 9028 and 9029 showed at least 50% inhibition of mRNA levels and are presently preferred.

Example 16 Screening of Antisense Oligonucleotides Complementary to Human PKC-ε

A series of 20-mer phosphorothioate oligonucleotides complementary to human PKC-ε were synthesized as described in Example 1. The source of the target sequence was Genbank locus HSPKCE, accession number X65293 (Burns et al.). These oligonucleotides were screened at a concentration of 500 nM for ability to decrease PKC-ε mRNA levels in human A549 cells, substantially as described in Example 6 using a Northern blot assay. The oligonucleotide sequences and results of the screen are shown in Table 12.

TABLE 12

INHIBITION OF mRNA EXPRESSION IN HUMAN A549 CELLS USING ANTISENSE OLIGONUCLEOTIDES COMPLEMENTARY TO PKC-E MRNA

| Oligo # | Sequence | Target region | % Inhib | Seq. ID |
|---|---|---|---|---|
| 7933 | ACTACCATGGTCGGGCGGG | AUG | 0 | 86 |
| 7934 | GTCCCACCGCATGGCGCAGC | Coding | 0 | 87 |
| 7935 | GTTTGGCCGATGCGCGAGTC | Coding | 0 | 88 |
| 7936 | TGCAGTTGGCCACGAAGTCG | Coding | 0 | 89 |
| 8032 | GTGGGGCATGTTGACGCTGA | Coding | 0 | 90 |
| 8031 | CCAGAGCAGGGACCCACAGT | Coding | 0 | 91 |
| 7939 | TCTCCTCGGTTGTCAAATGA | Coding | 0 | 92 |
| 7940 | CGGTGCTCCTCTCCTCGGTT | Coding | 0 | 93 |
| 7941 | AGCCAAAATCCTCTTCTCTG | Coding | 0 | 94 |
| 7942 | CATGAGGGCCGATGTGACCT | Coding | 62 | 95 |
| 7943 | ATCCCTTCCTTGCACATCCC | Coding | 4 | 96 |

TABLE 12-continued

INHIBITION OF mRNA EXPRESSION IN HUMAN A549 CELLS USING ANTISENSE OLIGONUCLEOTIDES COMPLEMENTARY TO PKC-E MRNA

| Oligo # | Sequence | Target region | % Inhib | Seq. ID |
|---|---|---|---|---|
| 7944 | CCCCAGGGCCCACCAGTCCA | Coding | 42 | 97 |
| 7945 | AGCACCCCAGGGCCCACCA | Coding | 56 | 98 |
| 7946 | CGTACATCAGCACCCCCAGG | Coding | 55 | 99 |
| 7947 | CCAGCCATCATCTCGTACAT | Coding | 15 | 100 |
| 7948 | TGCCACACAGCCCAGGCGCA | Coding | 55 | 101 |
| 7949 | TCAGGGCATCAGGTCTTCAC | Stop | 0 | 102 |
| 7950 | CTCTCAGGGCATCAGGTCTT | Stop | 0 | 103 |

In this experiment, oligonucleotides 7942, 7944, 7945, 7946 and 7948 showed at least 40% inhibition of mRNA levels and are presently preferred.

Example 17 DNA Sequencing of the 3' Untranslated Region of Human PKCα

A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.). Cells were harvested and total RNA was isolated using standard methods. Sambrook, J., Fritsch, E., and T. Maniatis (1989). Molecular Cloning: a laboratory manual. Cold Spring Harbor Laboratory, Cold Spring Harbor, N.Y., Ch. 7).

cDNA was made from the RNA using the 3' RACE technique of Frohman et al. [Frohman, M. A., Dush, M. K. and G. R. Martin (1988) Proc. Natl. Acad. Sci. U.S.A. 85:8998–9002] and the 3' RACE kit from Gibco/BRL (Bethesda, Md.). For making the first strand of cDNA, an oligo dT primer was used. For subsequent amplification from the site of the poly(A) tail, the oligonucleotide provided in the kit or an identical oligonucleotide (ISIS 5586; SEQ ID NO: 107: 5'-GGCCACGCGTCGACTAGTACTTTTTTTTTT TTTTT TT-3'). For amplification from the interior of the known sequence, ISIS 6288 was used (SEQ ID NO: 108: 5'-GGGGTAGAATGCGGCGGCAGTATGAAACTCACCA GCG-3'). The DNA resulting from the PCR reaction was gel-purified, digested with Sal I and Bcl I, and then cloned into the Bluescript plasmid (Stratagene, La Jolla, Calif.) using standard techniques (Sambrook et al., 1989). The cloned DNA was sequenced using a Sequenase Kit from USB.

The new sequence obtained, from the Bcl I site near the 3' end of the previously known sequence (GenBank accession number x52479) to the most frequently obtained site of polyadenylation is shown as nucleotides 56–1136 in FIG. 13. This site is believed to be the 3' end of the short (4 kb) PKCα message.

To extend this sequence and hence obtain sequences specific for the long PKCα message (8.5 kb), the technique of Inverse PCR was performed. Ochman, H., Gerber, A. S. and D. L. Hartl (1988) Genetics 120:621–623. This technique was performed three times using a three sets of primers and restriction enzymes. Each round resulted in about 200 bases of new sequence; the total of the new sequence (SEQ ID NO: 104) is shown in bold type (nucleotides 1137–1812) in FIG. 13. This sequence is shown extending in the 3' direction beginning at the Bcl I site (TGATCA) near the end of the previously published PKCα cDNA sequence. Finkenzeller et al., *Nucl. Acids Res.* 18:2183 (1990); Genbank accession number X52479. Newly determined sequences begin at nucleotide 56 and are underlined (SEQ ID NO:105). The most common site of polyadenylation, believed to be the 3' end of the short (4 kb) mRNA transcript, is at nucleotide 1136. Sequences downstream from this site, and therefore unique to the long message, are in bold (SEQ ID NO:106).

Example 18 Antisense Oligonucleotides Targeted to Novel Sequences in the 3' UTR of PKCα

A series of phosphorothioate antisense oligonucleotides, complementary to the novel sequence obtained as described in Example 17, were designed and synthesized. These oligonucleotides were screened on the basis of their ability to cause the reduction or elimination of PKCα RNA in A549 cells 24 hours after the start of treatment. A549 cells were treated with phosphorothioate oligonucleotides at 500 nM for four hours in the presence of the cationic lipids DOTMA/DOPE, washed and allowed to recover for an additional 20 hours. Total RNA was extracted and 20 µg of each was resolved on 1.2% gels and transferred to nylon membranes. These blots were probed with a $^{32}$p radiolabeled PKC-α cDNA probe and then stripped and reprobed with a radiolabeled G3PDH probe to confirm equal RNA loading. The two major PKC-α transcripts (8.5 kb and 4.0 kb) were examined and quantified with a PhosphorImager (Molecular Dynamics, Sunnyvale Calif.). The oligonucleotides and their activities are shown in Table 13.

TABLE 13

Inhibition of PKCα mRNA (both long and short) by phosphorothioate antisense oligonucleotides (500 nM) Expressed as percent of control mRNA level

| ISIS# | Sequence | Activity | Target region | SEQ ID NO: |
|---|---|---|---|---|
| 7416 | CAGTGCCCATGTGCAGGGAG | 100% | PKCα long mRNA | 109 |

TABLE 13-continued

Inhibition of PKCα mRNA (both long and short) by phosphorothioate antisense oligonucleotides (500 nM) Expressed as percent of control mRNA level

| ISIS# | Sequence | Activity | Target region | SEQ ID NO: |
|---|---|---|---|---|
| 7417 | AGAACCTGCACAAATAGAGC | 100% | PKCα long mRNA | 110 |
| 7418 | AGAAACAAGAACCTGCACAA | 100% | PKCα long mRNA | 111 |
| 7419 | GCAAGGGATTCAGCTAAAAC | 100% | PKCα long mRNA | 112 |
| 7420 | AGGGAGGGAAAGCACAGAAG | 100% | PKCα long mRNA | 113 |
| 7902 | AGGGAGGGAAAGCACAGAAG | 90% | PKCα long mRNA | 113 |
| 7907 | TCAGCTCAAAAATAGTCCTC | 85% | PKCα long mRNA | 114 |
| 7908 | CGAAAGGTGACATGAAGAAA | 100% | PKCα long mRNA | 115 |
| 7909 | GGCGGAGGAACCAGGACGAA | 90% | PKCα long mRNA | 116 |
| 7911 | GCAATGCCACGTGTGTACCA | 50% | PKCα long mRNA | 117 |
| 7912 | TGCAAAACGTATTAAAATCC | 100% | BKCα short mRNA | 118 |
| 7913 | TTATAAACATGCAAAATTCA | 100% | BKCα short mRNA | 119 |

ISIS 7911 (SEQ ID NO: 117) reduced PKCα mRNA levels (both long and short messages) in this preliminary experiment by 50% compared to control. This oligonucleotide is therefore preferred. Further analysis demonstrated that ISIS 7911 selectively reduced the amount of long (8.5 kb) message during the first six hours of treatment, with a fourfold selectivity at 3 hours post-treatment. By 12 hours after treatment with ISIS 7911, levels of both messages were reduced by over 80%. Time-course data are shown in FIG. 14.

What is claimed is:

1. An oligonucleotide up to 50 nucleotide units in length comprising a nucleotide sequence selected from the group consisting of SEQ ID NO:1, 2, 4, 5, 7, 8, 9, 10, 11, 12, 13, 14, 15, 16, 18, 19, 20, 52 and 53.

2. The oligonucleotide of claim 1 wherein at least one of the intersugar linkages between nucleotide units of the oligonucleotide is a phosphorothioate.

3. The oligonucleotide of claim 1 wherein at least one of the nucleotide units comprises a modification on the 2' position of the sugar.

4. The oligonucleotide of claim 1 which is a chimeric oligonucleotide.

5. An isolated nucleic acid molecule comprising the nucleotide sequence of SEQ ID NO:105.

6. The nucleic acid molecule of claim 5 wherein said nucleic acid molecule is double-stranded.

7. An isolated nucleic acid molecule comprising a sequence complementary to the nucleotide sequence of SEQ ID NO:105.

8. A polynucleotide probe up to 50 nucleotide units in length comprising a nucleotide sequence complementary to a portion of the nucleic acid molecule of claim 5 or claim 7.

9. An antisense oligonucleotide 5 to 50 nucleotides in length comprising a nucleotide sequence complementary to a portion of the sequence set forth in SEQ ID NO:105.

10. An antisense oligonuclcotide 5 to 50 nucleotides in length comprising a nucleotide sequence which is complementary to the long mRNA transcript of human protein kinase C-α and which is not complementary to the short mRNA transcript of human protein kinase C-α.

11. The anti sense oligonucleotide of claim 10 comprising a nucleotide sequence complementary to a portion of the sequence set forth in SEQ ID NO:106.

12. The oligonucleotide of claim 11 comprising a sequence as set forth in SEQ ID NO: 117.

13. A polynucleotide probe comprising a nuclcotide sequence complementary to the long mRNA transcript of human protein kinase C-α.

14. The polynucleotide probe of claim 13 comprising a sequence as set forth in SEQ ID NO: 117.

15. A method of inhibiting the expression of human protein kinase C-α in vitro comprising contacting human cells with a therapeutically effective amount of an antisense oligonucleotide 5 to 50 nucleotides in length, said antisense oligonucleotide comprising a nucleotide sequence complementary to a portion of the sequence set forth in SEQ ID NO: 105.

16. A method of inhibiting the expression of human protein kinase C-α in vitro comprising contacting human cells with a therapeutically effective amount of an antisense oligonucleotide 5 to 50 nucleotides in length, said antisense oligonucleotide comprising a nucleotide sequence complementary to a portion of the sequence set forth in SEQ ID NO: 106.

17. An oligonucleotide up to 50 nucleotide units in length comprising a nucleotide sequence selected from the group consisting of SEQ ID NO:3, 6 and 17.

18. The oligonucleotide of claim 17 wherein at least one of the nucleotide units comprises a modification on the 2' position of the sugar.

19. The oligonucleotide of claim 17 wherein at least one of the intersugar linkages between nucleotide units of the oligonucleotide is a phosphorothioate.

20. The oligonucleotide of claim 17 which is a chimeric oligonucleotide.

* * * * *

UNITED STATES PATENT AND TRADEMARK OFFICE
CERTIFICATE OF CORRECTION

PATENT NO. : 6,015,892
DATED : January 18, 2000
INVENTOR(S) : Bennett et al.

It is certified that error appears in the above-identified patent and that said Letters Patent is hereby corrected as shown below:

Column 2,
Lines 46 and 50, delete "PKC-η" and insert therefor -- PKC-ζ --;

Drawing,
In Sequence Description: SEQ. ID No. 104: (including the following) no.1020: (last column) please delete "GAATCACCA" and insert therefor -- GAATCAGGAA --;
no. 1080: (last column) please delete "TACGTTTTG" and insert therefor
-- TACGTTTTGC --;
no. 1140: (last column) please delete "AGTGAATAG" and insert therefor
-- AGTGAATAGA --;
no. 1200: (last column) please delete "TATAATAAA" and insert therefor
-- TATAATAAAC --;
no. 1260: (last column) please delete "GAGAGTATT" and insert therefor
-- GAGAGTATTA --;
no. 1320: (last column) please delete "CTAATCCTC" and insert therefor
-- CTAATCCTCT --;
no. 1380: (last column) please delete "GCACATGGG" and insert therefor
-- GCACATGGGC --;
no. 1440: (last column) please delete "ATGGCTAGT" and insert therefor
-- ATGGCTAGTT --;
no. 1500: (last column) please delete "TTGATTCTA" and insert therefor
-- TTGATTCTAC --;
no. 1560: (last column) please delete "CTTAGTTTC" and insert therefor
-- CTTAGTTTCT --;
no. 1620: (last column) please delete "ACAGGAAGT" and insert therefor
-- ACAGGAAGTG --;
no. 1680: (last column) please delete "CACCTGGGC" and insert therefor
-- CACCTGGGCT --;
no. 1740: (last column) please delete "GACTGTTGC" and insert therefor
-- GACTGTTGCT --;
no. 1800: (last column) please delete "GGACACGCA" and insert therefor
-- GGACACGCAG --;
In Sequence Description: SEQ. ID No. 105: (including the following) no. 1020: (last column) please delete "TTTAATACG" and insert therefor -- TTTAATACGT --;
no. 1080: (last column) please delete "TAACAAGTG" and insert therefor
-- TAACAAGTGA --;
no. 1140: (last column) please delete "ATGTTTATA" and insert therefor
-- ATGTTTATAA --;
no. 1200: (last column) please delete "ATAAAGAGA" and insert therefor
-- ATAAAGAGAG --;

UNITED STATES PATENT AND TRADEMARK OFFICE
CERTIFICATE OF CORRECTION

PATENT NO. : 6,015,892
DATED : January 18, 2000
INVENTOR(S) : Bennett et al.

It is certified that error appears in the above-identified patent and that said Letters Patent is hereby corrected as shown below:

no. 1260: (last column) please delete "TGTTTCTAA" and insert therefor
-- TGTTTCTAAT --;
no. 1320: (last column) please delete "TCCCTGCAC" and insert therefor
-- TCCCTGCACA --;
no. 1380: (last column) please delete "AATGAATGG" and insert therefor
-- AATGAATGGC --;
no. 1440: (last column) please delete "TGTATTTGA" and insert therefor
-- TGTATTTGAT --;
no. 1500: (last column) please delete "TCCCTCTTA" and insert therefor
-- TCCCTCTTAG --;
no. 1560: (last column) please delete "GGACAACAG" and insert therefor
-- GGACAACAGG --;
no. 1620: (last column) please delete "CGCAGCACC" and insert therefor
-- CGCAGCACCT --;
no. 1680: (last column) please delete "CCTGTGACT" and insert therefor
-- CCTGTGACTG --;
no. 1740: (last column) please delete "GTACTGGAC" and insert therefor
-- GTACTGGACA --;

Column 76,
Line 36, please delete "nuclcotide" and insert therefor -- nucleotide --;

Signed and Sealed this

Thirteenth Day of August, 2002

*Attest:*

JAMES E. ROGAN
*Attesting Officer*     *Director of the United States Patent and Trademark Office*